(12) United States Patent
Aerts et al.

(10) Patent No.: US 9,638,703 B2
(45) Date of Patent: May 2, 2017

(54) QUANTIFICATION OF GLUCOCORTICOIDS IN FISH SCALES AS BIOMARKERS FOR CHRONIC STRESS

(71) Applicants: Universiteit Gent, Ghent (BE); INSTITUUT VOOR LANDBOUW-EN VISSERIJONDERZOEK (ILVO), Merelbeke (BE)

(72) Inventors: Johan Aerts, Schilde (BE); Sarah De Saeger, Aalst (BE)

(73) Assignees: Universiteit Gent, Ghent (BE); INSTITUUT VOOR LANDBOUW-EN VISSERIJONDERZOEK, Merelbeke (BE)

( * ) Notice: Subject to any disclaimer, the term of this patent is extended or adjusted under 35 U.S.C. 154(b) by 0 days.

(21) Appl. No.: 15/105,550

(22) PCT Filed: Dec. 17, 2014

(86) PCT No.: PCT/EP2014/078117
§ 371 (c)(1),
(2) Date: Jun. 16, 2016

(87) PCT Pub. No.: WO2015/091591
PCT Pub. Date: Jun. 25, 2015

(65) Prior Publication Data
US 2016/0313355 A1 Oct. 27, 2016

(30) Foreign Application Priority Data

Dec. 19, 2013 (EP) .................................. 13198450
Jun. 17, 2014 (EP) .................................. 14172747

(51) Int. Cl.
*G01N 33/74* (2006.01)
*G01N 33/68* (2006.01)

(52) U.S. Cl.
CPC .......... *G01N 33/743* (2013.01); *G01N 33/68* (2013.01); *G01N 33/74* (2013.01); *G01N 2333/4603* (2013.01); *G01N 2800/7004* (2013.01)

(58) Field of Classification Search
CPC ...... G01N 33/743; G01N 33/68; G01N 33/74; G01N 2800/7004; G01N 2333/4603
See application file for complete search history.

(56) References Cited

FOREIGN PATENT DOCUMENTS

WO 2015091591 A1 6/2015

OTHER PUBLICATIONS

Barton, Bruce A., Stress in Fishes: A Diversity of Responses with Particular Reference to Changes in Circulating Corticosteroids, Integ. and Comp. Biol., 2002, pp. 517-525, vol. 42.

(Continued)

*Primary Examiner* — Jeremy C Flinders
(74) *Attorney, Agent, or Firm* — TraskBritt P.C.

(57) ABSTRACT

This disclosure relates to determining the stress level experienced by fish over a long period of time, which can be used in assessing the welfare status of fish. More, in particular, this disclosure relates to the usage of scales as well as other calcified tissue such as otoliths, spines and soft fin ray sampled from fish to quantify glucocorticoid levels in the scales/matrix. The levels of the glucocorticoids, such as cortisol or corticosterone, build up over time in scales and reflect long-lasting and stressful conditions that the fish have undergone during their lives and that have affected their level of stress. Hence, in vitro methods are disclosed herein that quantify the level of chronic stress in fish using scales as a logistic feasible, and non-invasive matrix for accurate and precise quantification of stress hormones.

13 Claims, 15 Drawing Sheets

(56) References Cited

OTHER PUBLICATIONS

Turner Jr., et al., Measurement of fecal glucocorticoids in parrotfishes to assess stress, General and Comparative Endocrinology, 2003, pp. 341-352, vol. 133.
Ellis et al., A non-invasive stress assay based upon measurement of free cortisol released into the water by rainbow trout, Journal of Fish Biology, 2004, pp. 1233-1252, vol. 65.
Scott et al., Measurement of fish steroids in water—a review, General and Comparative Endocrinology, 2007, pp. 392-400, vol. 153.
Bertotto et al., Alternative matrices for cortisol measurement in fish, Aquaculture Research, 2010, pp. 1261-1267, vol. 41.
Isermann et al., Estimating Black Crappie Age: An Assessment of Dorsal Spines and Scales as Nonlethal Alternatives to Otoliths, North American Journal of Fisheries Management, 2010, pp. 1591-1598, vol. 30.
Ellis et al., Cortisol and finfish welfare, Fish Physiol Biochem, 2012, pp. 163-188, vol. 38.
PCT International Search Report, PCT/EP2014/078117, dated Mar. 19, 2015.
PCT International Written Opinion, PCT/EP2014/078117, dated Mar. 19, 2015.
Lupica et al., Validation of enzyme-linked immunosorbent assay for measurement of faecal cortisol in fish, Aquaculture Research, 2009, pp. 437-441, vol. 40.
Pankhurst, N.W., The endocrinology of stress in fish: An environmental perspective, General and Comparative Endocrinology, 2011, pp. 265-275, vol. 170.
Simontacchi et al., Alternative stress indicators in sea bass *Dicentrarchus labrax*, L., Journal of Fish Biology, 2008, pp. 747-752, vol. 73.
Cirimele et al., Identification of ten corticosteroids in human hair by liquid chromatography—ionspray mass spectrometry, Forensic Science International, 2000, pp. 381-388, vol. 107.

US 9,638,703 B2

QUANTIFICATION OF GLUCOCORTICOIDS IN FISH SCALES AS BIOMARKERS FOR CHRONIC STRESS

CROSS-REFERENCE TO RELATED APPLICATIONS

This application is a national phase entry under 35 U.S.C. §371 of International Patent Application PCT/EP2014/078117, filed Dec. 17, 2014, designating the United States of America and published in English as International Patent Publication WO 2015/091591 A1 on Jun. 25, 2015, which claims the benefit under Article 8 of the Patent Cooperation Treaty to European Patent Application Serial No. 14172747.9 filed Jun. 17, 2014, and to European Patent Application Serial No. 13198450.2 filed Dec. 19, 2013.

TECHNICAL FIELD

This application relates generally to aquaculture and to determining the stress level experienced by fish, which can be used in assessing the chronic stress status of fish. More in particular, this disclosure relates to the usage of scales as well as other calcified tissues such as spines, soft fin ray and otoliths sampled from fish to quantify glucocorticoid levels in the scales and other matrices. The levels of the glucocorticoids—such as cortisol or corticosterone—build up over time in scales and reflect long-lasting and stressful conditions that the fish have experienced during their lives and that have affected their level of stress. Hence, in vitro methods are disclosed that quantify the level of chronic stress in fish using scales as a logistic feasible, and non-invasive matrix for accurate and precise quantification of the stress hormones.

BACKGROUND

Fish increasingly attract public, scientific and political interest around the world. Recreational and commercial fisheries are prominent in our societies; fish issues take a highly relevant position in discussions related to conservation biology (1) and environmental protection efforts (e.g., effects of climate change, novel predators, novel animal-environment relationships on stress and as a consequence on fitness) (2, 3). Anthropogenic activities (e.g., energy production, shipping traffic, industrial pollution) compromise wild stocks (4). Therefore, various international monitoring schemes aim to scientifically clarify their impact on the health status of oceanic niches. A similar situation exists for freshwater stocks as they are under threat by soil erosion, fertilizers, etc., as agriculture expands. The human population keeps on expanding, making the need for a sustainable food production a prime global priority. Fish protein is one of the most important protein sources for human consumption. Now that fisheries meet limits in yield, aquaculture expands rapidly worldwide and puts increasing pressure on farmers to produce in an optimal, sustainable and animal-friendly way (5, 6). High numbers of fish (e.g., zebrafish and medaka) are used as vertebrate models and alternatives to rodents in biomedical research (e.g., in bone physiological research). The imperative to maintain research-driven innovation in this sector, while global economic output dwindles, adds to exploitation of fish. In the recent past, ethics concerning fish suffering and welfare urge more attention as high numbers of fish are involved in fisheries (7), the rapidly growing and intensifying aquaculture industries (8, 9), public aquaria (10, 11) and scientific research laboratories (12).

Appreciating and understanding fish biology as basis for management, control and decision-making in fish exploitation puts a phenomenal challenge to those involved, coming from a multitude of disciplines (from molecular biology to eco-physiology), viewing from multiple angles (all different stakeholders) and representing highly specific and cherished expertise. In this framework, new scientifically validated biomarkers to assess levels of stress in fish, in particular, of chronic stress, are of utmost importance.

Fish welfare easily becomes compromised, and consensus is growing that proper welfare assessment requires animal-based, physiological indicators being superior to less consistent, indirect husbandry-related parameters such as water quality. However, a shortage exists on practical, reliable and validated biomarkers for chronic stress. A frequently used, seemingly logical biomarker for fish is the blood level of the "stress steroid" cortisol. Fish faced with stressful stimuli launch an endocrine stress response through activation of the hypothalamic-pituitary-interrenal (HPI-) axis to release cortisol (13, 14) into the blood. Cortisol elicits a suite of physiological and behavioral changes (15-17) that allow the fish to cope with altered situations (18-20). The adaptive value of short-term cortisol actions is widely recognized (21, 22). Far less is known about persistent stress and its mostly detrimental consequences for health, growth, and reproduction (19, 20). Definition of a robust, easily performable and scientifically validated chronic stress biomarker is thus of utmost importance. Glucocorticoid levels in plasma of fish show diet variation (23), do not reveal the lifetime exposure of the fish to stress, and provide no more than a snapshot of the cortisol status at the moment of sampling (24, 25). Moreover, blood sampling is invasive and unavoidably causes confounding stress to the fish because of netting, air exposure and handling. This makes plasma cortisol prone to bias as levels rise rapidly a few minutes after confrontation with a stressor (13). Anesthetics adopted to facilitate blood sampling may, by themselves, reduce or block the activation of the HPI-axis, thereby affecting the cortisol release in blood and resulting in erroneous results (26, 27). Restrictions also apply to the assay of cortisol in alternative matrices such as mucus (28, 29), gut content (29), feces (30) and water (31, 32). The pertinent literature lacks data on cortisol in a matrix suitable for chronic stress evaluation. Hitherto, the majority of studies addressed cortisol only, and reports on glucocorticoid production pathway(s) (33) or their significance in chronic stress are scarce. Fish record (a-)biotic events and store this history in calcified tissues (34-37). As feathers of birds (38) and hair of mammals (39), the ideal matrix for chronic stress assessment in fish should at least meet the following criteria: (i) incorporation of glucocorticoids; (ii) slow but persistent growth; and (iii) ease in sampling.

Elasmoid scales, calcified dermal exoskeletal structures (40), grow along with the fish and consist of an acellular collagenous matrix, which is mineralized with calcium hydroxyapatite on the outer layer and lined with a monolayer of cells with osteoblast- and osteoclast-like properties. Upon removal, a scale will regenerate within days (41). Scales are a target for endocrine stimuli. A high affinity, low-capacity estradiol-17b binding was found in scleroblast cytosol of rainbow trout (*Oncorhynchus mykiss*) (42) and estrogen receptors have immunohistochemically been detected in Mozambique tilapia (*Oreochromis mossambicus*) and gilthead sea bream (*Sparus auratus*) scales (43). A scale is easily and quickly collected with negligible injury and stress to the fish without confounding its cortisol levels due to the sampling procedure.

SUMMARY

This disclosure relates to determining the stress level experienced by fish over a long period of time, which can be used in assessing the welfare status of fish. More, in particular, this disclosure relates to the usage of scales as well as other calcified tissue such as otoliths, spines and soft fin ray sampled from fish to quantify glucocorticoid levels in the scales/matrix. The levels of the glucocorticoids, such as cortisol or corticosterone, build up over time in scales and reflect long-lasting and stressful conditions that the fish have undergone during their lives and that have affected their level of stress. Hence, in vitro methods are disclosed herein that quantify the level of chronic stress in fish using scales as a logistic feasible, and non-invasive matrix for accurate and precise quantification of stress hormones.

DETAILED DESCRIPTION

Figure 1:
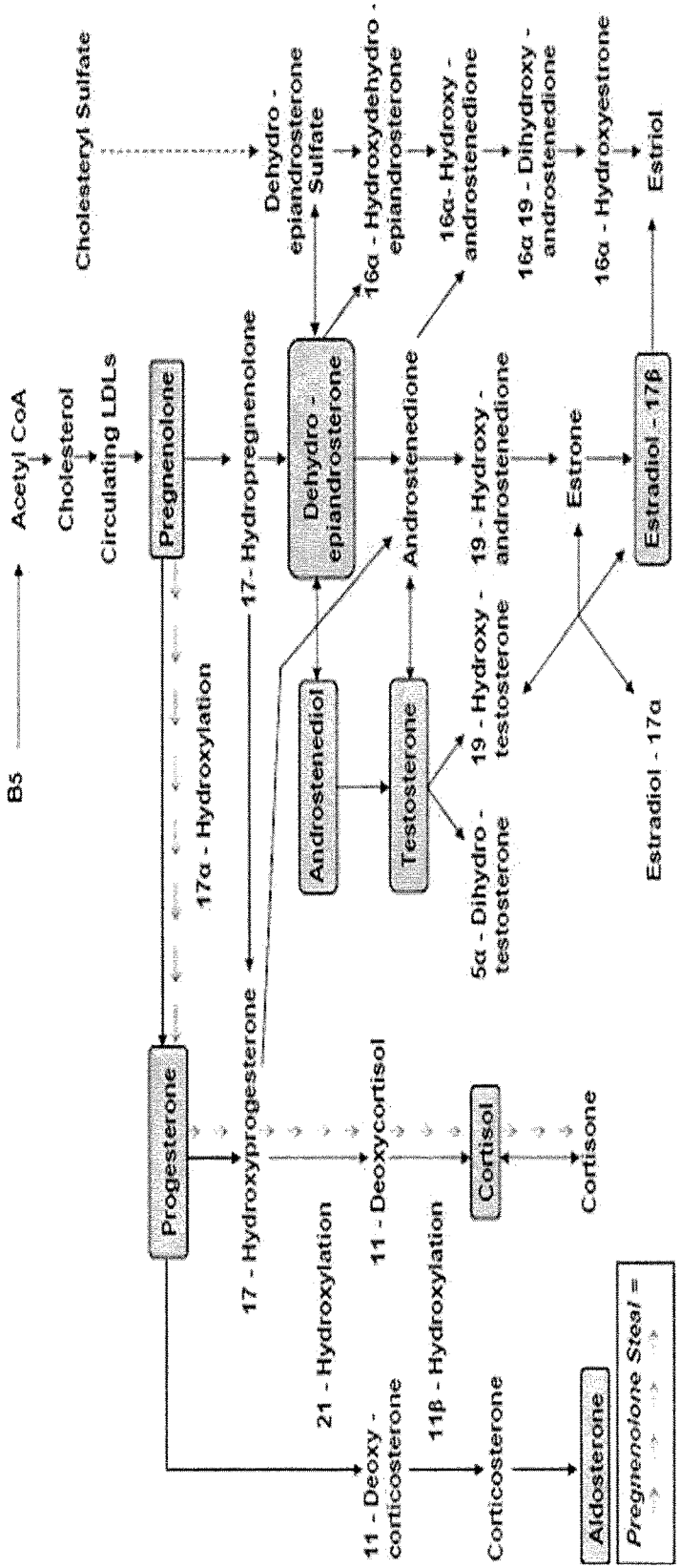
FIG. 1: Steroidal hormone principle pathways and analytes involved in the chronic stress response.[44]
Figure 2:
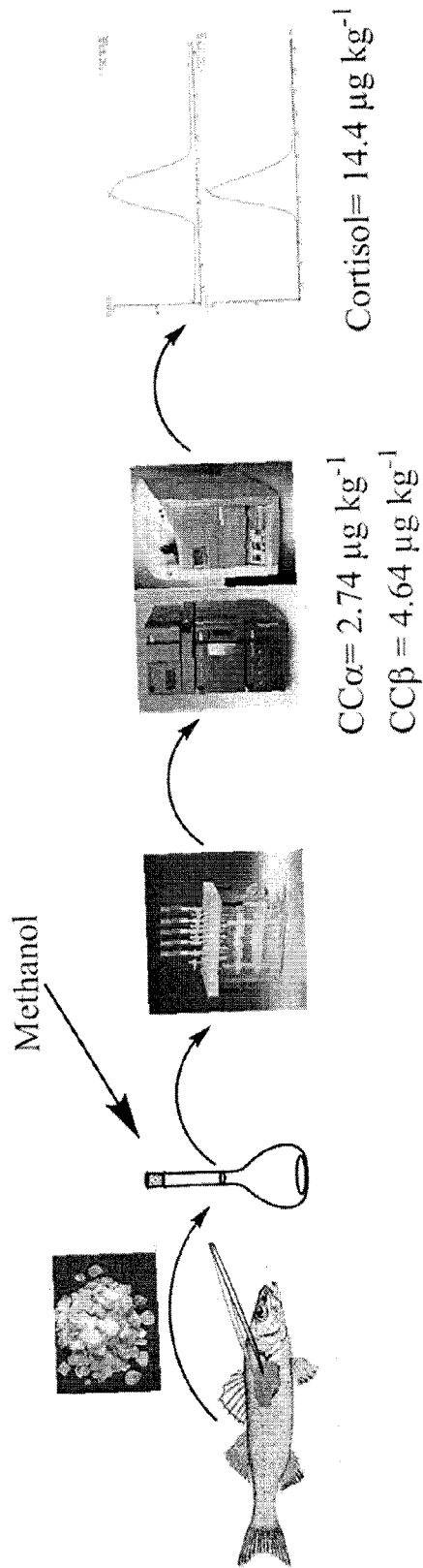
FIG. 2: Schematic overview of the method.

This disclosure relates to the finding that the glucocorticoid profile in fish is captured in scales, and that glucocorticoid levels in these dermal bone plates reflect a time-integrated sample of the degree of stress the fish experienced over time. Scales are indeed considered as an ideal matrix for chronic stress monitoring in fish as scales are easily sampled in a non-invasive manner and as scales allow convenient sample preparation for further quantification of glucocorticoid levels in the scales. This disclosure thus relates to accurate, precise and robust methods for quantification of glucocorticoids such as cortisol in fish scales to assess exposure of the fish to stress during an extended period of time.

More specifically, this disclosure relates to an in vitro method to quantify the level of chronic stress in a fish comprising:
obtaining at least one scale from the fish,
extracting glucocorticoids from the scales,
purifying the glucocorticoids extracted from the scales,
quantifying the purified glucocorticoids, and
correlating the quantified glucocorticoids with a level of chronic stress.

The term "glucocorticoids" means cortisol when (elasmoid) scales are taken from a fish (Pisces) belonging to the infraclass Teleostei, and/or, means "corticosterone" when (ganoid) scales are taken from a fish belonging to the class Chondrichtyes, and/or means, when the detection of possible extra-interrenal pathways is additionally required, "precursors of cortisol," such as 17α-hydroxyprogesterone and/or 11-deoxycortisol and/or "precursors of corticosterone," such as 11-deoxycorticosterone, and/or means "metabolites of cortisol," such as cortisone, Reichstein's U (or 20-dihydrocortisone), tetrahydrocortisol and/or tetrahydrocortisone and/or "metabolites of corticosterone," as these metabolites may influence the glucocorticoid levels in the scales so that their detection is additionally required.

The chemical structure of the above-indicated glucocorticoids is the following[45]:

Cortisol or 11β,17α,21-trihydroxypregn-4-ene-3,20-dione:

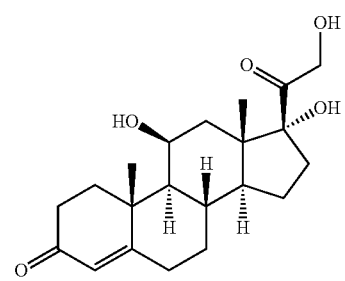

Corticosterone or 11β,21-Dihydroxy-4-pregnene-3,20-dione:

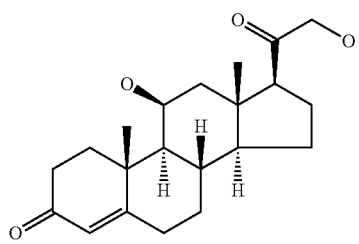

17α-Hydroxyprogesterone or 17α-Hydroxypregn-4-ene-3,20-dione:

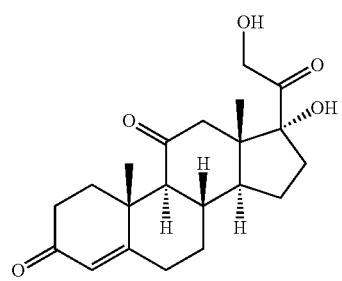

Reichstein's U or 20-dihydrocortisone or 17a,20,21-trihydroxy-pregn-4-een-3,11-dion

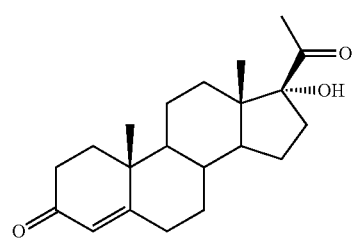 [SMILES: CC(=O)[C@@]1(O)CCC2C3CCC4=CC(=O)CC[C@]4(C)C3CC[C@@]21C]

11-Deoxycortisol or 17α, 21-Dihydroxypregn-4-ene-3, 20-dione:

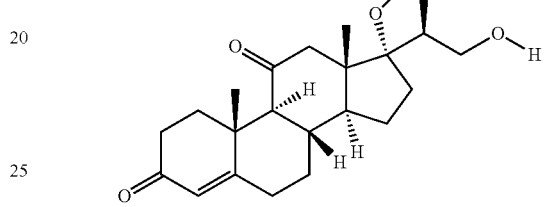

Tetrahydrocortisol or 3α,11β,17α,21-tetrahydroxy-5β-pregnaan-20-on:

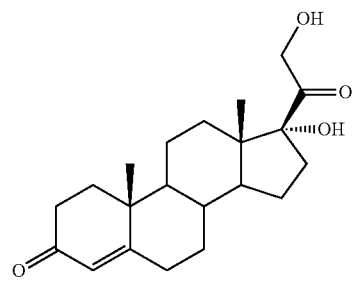 [SMILES: C[C@]12CCC(=O)C=C1CCC1C2CC[C@@]2(C)C1CC[C@]2(O)C(=O)CO]

11-Deoxycorticosterone or 21-hydroxypregn-4-ene-3,20-dione

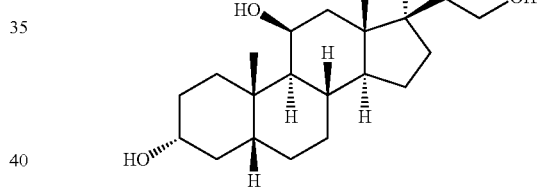

Tetrahydrocortisone or 3α,17α,21-trihydroxy-5f3-pregnaan-11. 20-dion:

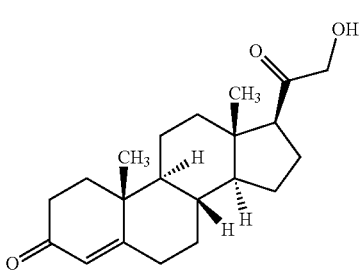

Cortisone or 17α,21-Dihydroxy-pregn-4-een-3,11,20-trion:

Hence, this disclosure relates to a method as described herein, wherein the glucocorticoids are cortisol, 17α-hydroxyprogesterone, 11-deoxycortisol, corticosterone, 11-deoxycorticosterone cortisone, Reichstein's U, tetrahydrocortisol and/or tetrahydrocortisone. As the classical parameter considered to reflect the stress response in teleost fish, cortisol is released into the bloodstream making incorporation in calcified structures possible and hereby a prime target analyte for chronic stress research. Its precursors 17α-hydroxyprogesteron and 11-deoxycortisol were included in the method to unravel the existence of possible extra-interrenal pathways. As the existence of extra-interrenal pathways in fish are at present not known, but as there are indications of extra-adrenal pathways in humans[46], both analytes were incorporated in the method for future research purposes. The existence of such a pathway could have a profound effect on our understanding of the HPI-axis and as a consequence stress. The metabolites cortisone, Reichstein's U, tetrahydrocortisol and tetrahydrocortisone were also included in the method as exogenous glucocorticoids in the water (coming from other fish, anthropogenic activities, etc.) may act as an endocrine disruptor possibly influencing the glucocorticoid profile in the scales.

The term "fish" means, in essence, any gill-bearing, craniate aquatic animal that has scales but specifically refers to fish belonging to the taxonomic class of the Chondrichtyes (cartilaginous fish) or to the taxonomic infraclass of Teleostei (bony fish).

This disclosure further specifically relates to a method as described above, wherein the fish belong to the infraclass of Teleostei.

More specifically, the disclosure relates to a method as described above wherein the fish belonging to the infraclass of Teleostei are fish belonging to the family Moronidae (e.g., European Sea bass), the family Sparidae (e.g., Sea breams), the family Soleidae (e.g., *Solea solea* and *Solea senegalensis*), the family Salmonidae (e.g., salmon, trout), the so-called Kingfish (e.g., Yellow tail Kingfish), the family Scombridae (e.g., Tuna), the family Gadidae (e.g., Cod), the family Cyprinidae (e.g., common carp, koi carp), and cichlid fish (e.g., Mozambique as well as Nile tilapia).

The term "scale" means dermal bone plates typically found in fish skin that display growth-dependent concentric rings or annuli. More specifically, the term "scale" refers to an "elasmoid scale" as found in Teleostei and refers to a "ganoid scale" as found in Chondrichtyes.

The term "chronic stress" in fish means stress buildup over time and reflecting long-lasting and stressful conditions due to handling, poor water quality, stocking density, predation and several other antropogenic factors such as windmills, boat traffic, touching, etc. Chronic stress is thus a long-lasting condition from which fish cannot fully recover. The direct effects of the stress factors, as well as changes occurring at the endocrinological level, immune system or function level can be responsible for (pre)pathological consequences, which reduce welfare of the fish.

The term "obtaining scales from a fish" means removing at least one scale from the skin of a (living or dead) fish with, for example, fine tweezers. The scales can be taken from any part of the body of the fish, i.e., dorsal, cranioventral, medioventral, caudal, left or right side, etc. To standardize the method of this disclosure, scales were taken from the mediodorsoventral zone dorsally to the pectoral fin. This non-invasive manner of sample collection has no effect on the fish as the removed scales regrow within a short period of time. These regenerated scales were proven to exhibit the same incorporation profile of glucocorticoids in terms of experienced stress and provide, as such, an additional tool to quantify chronic stress in a well-defined time frame.

As the weight of a single scale depends on the fish species as well as on the age of the fish, with smaller scales in juvenile fish, the number of scales needed depends on both of these factors. For this reason, the method of the disclosure was standardized, using a standardized amount of scales corresponding to, for example, 100 mg of scales, though tests point out that smaller amounts (such as 80, 60, 40, 20, 10, 5, 1 mg, etc., of scales) can be used as well. The number of scales corresponding to 100 mg of scales is often about 40 to 80 scales, such as 60 scales, but it should be clear that the method of this disclosure can be performed using 1, 2, 3, 4, 5, 6, 7, 8, 9, 10 or more scales, taking into account both factors as mentioned above.

Thus, this disclosure also relates to a method as described above, wherein obtaining at least one scale from the fish is obtaining between 40 and 80 scales from the fish.

The term "extracting glucocorticoids from the scale" relates to any method to separate/extract glucocorticoids from the scales. Typical, but non-limiting, extraction methods of the disclosure involve the extraction of glucocorticoids out of an aqueous phase and into an organic phase. Extraction solvents that can, for example, be used are methanol, 2-propanol, acetonitrile, diethyl ether, etc. Methanol, however, is a preferred solvent.

Hence, this disclosure relates to a method as described above, wherein extracting glucocorticoids is undertaken by adding methanol as the extraction solvent. An example of an extraction of the disclosure is as follows: of the homogenized scale sample, 0.1 g±0.001 g is weighed into a 10 ml test tube. Subsequently, 8 ml of methanol is added as extraction solvent and 10 μL of a cortisol-$d_4$ solution of 0.5 μg $L^{-1}$ is added as internal standard. The sample is vortex-mixed for 30 seconds, placed on an overhead shaker at 60 rpm for 1 hour at room temperature and centrifuged for 10 minutes at 3500 g at 7° C. All supernatant is taken, evaporated to dryness under nitrogen at 60° C. using a nitrogen evaporator, and reconstituted in 5 ml $H_2O$/MeOH (80:20; v/v) for subsequent Solid Phase extraction (SPE).

The term "purifying the glucocorticoids extracted from the scale" relates to any method to render the glucocorticoids of this disclosure pure or more pure, as well as concentrated or more concentrated, and/or to eliminate impurities as much as possible.

More in particular, this disclosure also relates to a method as described above, wherein the extraction with methanol is followed by an SPE (solid phase extraction). A non-limiting example of a purification step of the disclosure is as follows: after conditioning a C18 SPE column with 3 ml of methanol followed by 3 ml of ultrapure water, a sample as obtained above is loaded. The column is washed with 4.5 ml $H_2O$/MeOH (65:35; v/v) and retained compounds are eluted with 2.5 ml $H_2O$/MeOH (20:80; v/v) into a 10 ml test tube and evaporated to dryness under nitrogen at 60° C. using a nitrogen evaporator. The sample is finally reconstituted in 100 μL $H_2O$/MeOH (80:20; v/v) in a vial and analyzed by means of ultra-performance liquid chromatography coupled to tandem mass spectrometry (UPLC-MS/MS).

The term "quantifying the purified glucocorticoid" refers to any method to determine the amount of glucocorticoids obtained after extraction/purification as described above.

More specifically, this disclosure relates to a method as described above, wherein quantifying of extracted and purified glucocorticoids is undertaken by liquid chromatography coupled to tandem mass spectrometry ((U)HPLC-MS/MS),[47-48] high performance liquid chromatography coupled to ultraviolet detection (HPLC-UV) and Diode Array Detection (HPLC-DAD),[49-50] or fluorescence detection (HPLC-FL),[51-52] gas chromatography (GC),[53-54] a (radio)(enzymatic)immunoassay (RIA)[55-56] (EIA)[57-58] or a sensor-based technique.[59-60]

This disclosure also relates to a method as described above, wherein the liquid chromatography coupled to tandem mass spectrometry is ultra-performance liquid tandem mass spectrometry.

More specifically, this disclosure relates to a method as described above, wherein the immunoassay is a radio immunoassay or an enzyme immunoassay.

The term "correlating the quantified glucocorticoids with a level of chronic stress" refers to the fact that stressed teleost fish produce cortisol, which is released into the bloodstream. When this stress load is prolonged in time, cortisol circulates during this prolonged period in the blood. Taking into account the structure of a scale, a certain percentage of this bioactive and free-circulating cortisol is incorporated into the scale. As scales grow in time, this gives the opportunity to quantify the cortisol and thus the stress load in time. Knowing this, scales of fish exposed to a varying stress load can be analyzed for glucocorticoids. For example, fish that are exposed to a minor stress load (i.e., confinement into a reduced volume (such as 25% of the "original" volume) for 30 minutes every 2nd day) have an average cortisol amount of 1.70 $\mu g\ kg^{-1}$, while this is 3.44 $\mu g\ kg^{-1}$ in highly stressed fish (i.e., confinement into 10% volume for 30 minutes, +chasing 5 minutes every 2nd day, +air exposure for 1 minute once per week).

The disclosure thus relates in essence to the usage of fish scales sampled from a fish to determine or quantify the level of chronic stress of the fish.

This disclosure relates to the usage as described above wherein quantification/determination is undertaken by a method according to the methods described above.

Scales are the most important matrix for chronic stress quantification as they are collected in a non-invasive manner. However, other calcified matrices such as otoliths, spines and fin rays may, in certain circumstances, be used as well as matrices for chronic stress quantification. The latter quantification can be undertaken in the same manner as described above for scales. In particular, spines and fin ray are cut off with scissors and homogenized by cutting them into small pieces, while otoliths are removed with a scalpel and homogenized by grinding using a mortar.

Soft fin rays are flexible, segmented and branched at the distal part elongating by adding a new segment to the tip. Spines are not segmented but fused from the base and exhibit a continuous growth. Otoliths are part of the organs of balance in the inner ear and primarily composed of crystallized calcium carbonate in the form of aragonite and of a fibrous, collagen-like protein called otoline. They display easily discernible daily increments that are deposited radially and maintained when somatic growth is non-existent. Soft fin rays and scales may regenerate rapidly when they are lust or damaged.

Thus, this disclosure further relates to the usage of the other calcified matrices such as a spine, a fin ray or an otolith sampled from a fish to quantify the level of chronic stress of the fish.

The disclosure thus also relates to an in vitro method to quantify the level of chronic stress in a fish comprising:
  obtaining at least one spine, fin ray or otolith from the fish,
  extracting glucocorticoids from the spine, fin ray or otolith,
  purifying the glucocorticoids extracted from the spine, fin ray or otolith,
  quantifying the purified glucocorticoids, and
  correlating the quantified glucocorticoids with a level of chronic stress.

The disclosure will now be illustrated by the following non-limiting examples.

Example 1

Development and Validation of a UPLC-MS/MS Method for Quantifying Glucocorticoids in Scales of European Sea Bass (*Dicentrarchus labrax*)

Methods and Materials
Instrumentation, Materials, and Reagents

Chromatographic analysis was performed on an ACQUITY UPLC-MS/MS Premier XE using an ACQUITY ULTRA PERFORMANCE LC® BEH C18 (1.7 µm; 2.1×100 mm) column (Waters, Milford, USA). Samples were evaporated to dryness with a TURBOVAP® nitrogen evaporator (Biotage, Sweden). Grace Pure™ SPE C18-Max (500 mg, 6 ml) columns for solid-phase extraction (SPE) were obtained from Grace Davison Discovery Sciences (Lokeren, Belgium). High-performance liquid chromatography (HPLC)-gradient grade methanol (Hipersolv Chromanorm) as extraction solvent was obtained from VWR International BVBA (Leuven, Belgium), while methanol absolute LC-MS as well as formic acid ULC-MS grade from Biosolve BV (Valkenswaard, The Netherlands) and ultrapure water of a MILLI-Q® gradient Q-GARD® 2 from Millipore (Billerica, USA) were used as mobile phase solvents.

Compounds, Standards, and Solutions

Only products with certificate of analysis were used. Cortisol, cortisone, 17α-hydroxyprogesteron, and 11-deoxycortisol were from Sigma-Aldrich (Diegem, Belgium). Tetrahydrocortisol and tetrahydrocortisone were from Sequoia Research Products Ltd (Pangbourne, United Kingdom). Cortisol-$d_4$ from CDN Isotopes (Pointe-Claire, Canada) was used as an internal standard.

Individual stock standard solutions of 1 mg $mL^{-1}$ of all compounds and internal standard were prepared in methanol and stored at 4° C. Calibration standards, ranging from 0.005 mg $L^{-1}$ to 0.1 mg $L^{-1}$, were prepared by addition of 10 µl of a cortisol-$d_4$ solution of 0.5 µg $L^{-1}$ to 0.5 µL, 2.5 µL, 5 µL, and 10 µL of a standard solution of 1 µg $L^{-1}$ in 100 µL of $H_2O$/MeOH (80:20; v/v), respectively. As 100 mg of sample were used, this corresponded to a range from 5 µg $kg^{-1}$ to 100 µg $kg^{-1}$ in matrix.

Sampling

All calcified structures were sampled from sacrificed European sea bass (*Dicentrarchus labrax*) were deeply anesthetized with 2-phenoxyethanol and killed by spinal transection. All fish weighed around 100 g. Sixty scales from the left mediodorsoventral zone dorsally to the pectoral fin were removed from the skin with fine tweezers. Four dorsal spines and six soft fin rays from the caudal fin were retrieved using scissors. Two sagittal otoliths were taken from the opened skull. All samples were rinsed with ultrapure water and air dried on a paper tissue at room temperature.

Sample Preparation

Scales, spines, and soft fin rays were cut into fine pieces using scissors. Otoliths were ground in a mortar. Scissors and mortar were rinsed with ethanol followed by ultrapure water and dried with a paper tissue. Of the homogenized sample, 0.1 g±0.001 g was weighed in a 10 ml test tube. Subsequently, 8 ml of methanol was added as extraction solvent and 10 µL of a cortisol-$d_4$ solution of 0.5 µg $L^{-1}$ was added as internal standard. The sample was vortex-mixed for 30 seconds, placed on an overhead shaker at 60 rpm for 1 hour at room temperature and centrifuged for 10 minutes at 3500 g at 7° C. All supernatant was taken, evaporated to dryness under nitrogen at 60° C. using a nitrogen evaporator, and reconstituted in 5 ml $H_2O$/MeOH (80:20; v/v). After conditioning, a C18 SPE column with 3 ml of methanol followed by 3 ml of ultrapure water, sample was loaded. The column was washed with 4.5 ml H$_2$O/MeOH (65:35; v/v) and retained compounds were eluted with 2.5 ml H$_2$O/MeOH (20:80; v/v) into a 10 ml test tube and evaporated to dryness under nitrogen at 60° C. using a nitrogen evaporator. The sample was finally reconstituted in 100 µL H$_2$O/MeOH (80:20; v/v) in a vial and analyzed by means of UPLC-MS/MS.

LC-MS/MS Analysis

Glucocorticoids were separated using a gradient elution of mobile phases A and B. Mobile phase A was a mixture of ultrapure water with 0.1% formic acid, while mobile phase B was a mixture of methanol with 0.1% formic acid. Initially, gradient elution started at 20% (v/v) of mobile phase B. Subsequently, mobile phase B was increased to 56% at 1.5 minutes, to 63% at 6.5 minutes, to 99.1% at 7.5 minutes, after which it was kept at 99.1% to 8 minutes, and finally decreased to 20% at 9 minutes and kept in this way to 10 minutes. The flow rate was kept constant at 0.4 ml minute$^{-1}$, resulting in a 10-minute running time. Samples were cooled at 7° C. in the autosampler. The injection volume was set at 40 µL, while the column temperature was maintained a 30° C.

Chromatographic analysis was performed on a mass spectrometer used in the multiple reactions monitoring (MRM) mode in order to achieve optimal sensitivity and selectivity. For every target analyte, two precursor fragment ion transitions were determined. Instrumental parameters were optimized by the direct infusion of 10 µg L$^{-1}$ standard solution in methanol+0.1% formic acid at a flow rate of 10 µL minute$^{-1}$. The use of two precursor fragment ion transitions allowed the determination of the ratio between both transitions, which was used together with the relative retention time for the identification and confirmation of the identity of each analyte according to the requirements of the Commission Decision No. 2002/657/EC.[61] The mass spectrometer was used in positive electrospray ionization mode (ESI$^+$). All compounds were analyzed as their proton adducts [M+H]$^+$. The MS detector settings were set at the following values: a source temperature of 120° C., a de-solvation temperature of 300° C. at a gas flow of 800 L h$^{-1}$, a cone gas flow of 50 L h$^{-1}$, and a capillary voltage of 3 kV. Argon was used as collision gas at a pressure of 1.11. 10$^{-2}$ mbar. The optimized UPLC-MS/MS conditions with indication of retention time, precursor ion, product ions, cone voltage, and collision energy for all compounds are given in Table 1.

TABLE 1

Optimized UPLC-MS/MS conditions per compound

| Compound | Retention time (minute) | Precursor ion (m/z) | Fragment ion-quantification* and qualification trace (m/z) | Cone voltage (V) | Collision energy (eV) |
|---|---|---|---|---|---|
| 20-Dihydrocortisone | 2.80 | 363.3 | 163.00* | 35 | 25 |
|  |  |  | 267.20 |  | 22 |
| Cortisone | 2.88 | 361.2 | 121.00* | 45 | 37 |
|  |  |  | 163.00 |  | 24 |
| Cortisol-d$_4$ | 3.14 | 367.2 | 121.10* | 35 | 20 |
|  |  |  | 331.30 |  | 18 |
| Cortisol | 3.15 | 363.2 | 121.10* | 35 | 20 |
|  |  |  | 327.30 |  | 18 |
| 11-Deoxycortisol | 3.95 | 347.2 | 97.10* | 40 | 25 |
|  |  |  | 109.10 |  | 30 |
| Tetrahydrocortisol | 4.26 | 367.1 | 313.20* | 20 | 10 |
|  |  |  | 331.30 |  | 10 |
| Tetrahydrocortisone | 4.49 | 365.1 | 329.20* | 30 | 15 |
|  |  |  | 347.20 |  | 12 |
| 17α-Hydroxyprogesteron | 5.66 | 331.2 | 97.00* | 35 | 25 |
|  |  |  | 109.10 |  | 25 |

Data analysis was performed using Quan/Targetlynx software from Waters; analysis results were reported as the value (µg kg$^{-1}$)±the expanded measurement uncertainty (µg kg$^{-1}$) with a coverage factor (k) of 2 (95% confidentiality interval).

Validation

Validation samples for every calcified structure were made by pooling of scales, spines, soft fin rays, and otoliths from 51, 51, 57, and 118 fish, respectively, reared under similar conditions. No certified reference material, inter-laboratory comparison tests or any other validated methods for the above-mentioned analyte/matrix combinations exist and, therefore, validation was done using standard addition to validation samples. For every calcified structure, five concentration levels, ranging from 1 to 50 µg kg$^{-1}$, were tested in five-fold and this was repeated on four different days within a period of one month under intra-reproducibility conditions, i.e., by two persons using different solutions and one UPLC-MS/MS system. All validation experiments were carried out by authorized personnel in controlled environment with calibrated equipment and controlled solutions according to the requirements of the standard EN ISO/IEC 17025:2005.[62] Analysis was done using standardized sequences consisting of different calibration standards, blanks, negative and positive controls (all in diluent). Results for every compound were evaluated by assessing the (relative) retention time and relative ion intensities of the compound and fragments. All validation parameters were determined and evaluated according to the requirements of the Commission Decision No. 2002/657/EC: trueness, precision, working range, linearity, decision limit (CCα), detection capability (CCβ), sensitivity, and selectivity.

The apparent recovery, as well as precision (repeatability and intra-laboratory reproducibility), for all compounds were determined under intra-reproducibility conditions resulting in 20 analyses for every concentration level and a total of 100 analyses per compound and matrix. Due to the low concentration levels, a Dixon's outlier test,[63] as well as a Grubbs,[64] test were performed to detect possible outliers. The decision limit (CCα) was calculated as the intercept of the calibration curve plus 2.33 times the standard deviation on the intra-laboratory reproducibility ($\alpha=1\%$), while the detection capability (CCβ) was calculated as the concentration of CCα plus 1.64 times the standard deviation on the intra-laboratory reproducibility ($\beta=5\%$). The expanded measurement uncertainty was based on the validation data for trueness and intra-laboratory reproducibility and determined using two different approaches, by linear summation and by quadratic summation or Nordtest method. In addition, the robustness of the method and stability of the analytes in diluent, as well as in matrix, were monitored during method development. Finally, the expanded measurement uncertainty was determined by linear summation as well as by quadratic summation or Nordtest method[47-52] (there is no consensus in the literature on a preferred method).

Results

A UPLC-MS/MS quantification method for cortisol, its precursors 17α-hydroxyprogesterone and 11-deoxycortisol, cortisone and key metabolites tetrahydrocortisol and tetrahydrocortisone in fish scales was developed in an EN ISO/IEC 17025:2005 accredited environment and validated according to the requirements of the Commission Decision No. 2002/657/EC. As the classical parameter considered to reflect the stress response in most fish, cortisol is released into the bloodstream making incorporation in calcified structures possible and hereby a target analyte for chronic stress research. Its precursors, 17α-hydroxyprogesteron and 11-deoxycortisol, were included in the analyses to cover detection of possible extra-interrenal pathways. The metabolites tetrahydrocortisol and tetrahydrocortisone were also included as exogenous glucocorticoids (in the water) may act as endocrine disruptor and influence the glucocorticoid profile of the calcified structures studied. The method was tested and validated for spine, soft fin ray, and otolith as well. The convenience of scale sampling is addressed.

Method Development

Sampling and Sample Preparation

For each calcified structure, the location for sampling was determined. Scales are mesodermal skeletal elements in post-metamorphosis fish. No differences were found in cortisol content in scales taken from the various sides (e.g., dorsal, cranioventral, medioventral, or caudal) of the fish nor between scales taken from the left and right side. Scales for the lateral line should be avoided as they differ in structure. For ease and future research purposes (taking into account the applicability in aquaculture), scales were chosen from the mediodorsoventral zone dorsally to the pectoral fin. Spines in sea bass are found among others in the cranial part of the first dorsal fin (8 to 10 spines). Spines are not segmented, but fuse at the base and are, therefore, more rigid than soft fin rays. A higher concentration of glucocorticoids was found in spines at their base, which requires better fine-tuning of cortisol incorporation over time in this tissue. In addition, all except the distal parts of the spine are covered by epithelium. No differences were found in cortisol content in soft fin rays taken from the dorsal, cranioventral, medioventral, and caudal fins. Taking into account the applicability in aquaculture, soft fin rays were chosen from the caudal fin. Sagittal otoliths were chosen as they are the largest and easiest to remove.

With respect of an optimal combination of logistic feasibility and analytical performance, the optimal amount of matrix for analysis was determined for each calcified structure by spiking different amounts of sample, i.e., different number of scales, spines and soft fin rays from the same fish, with 5 µg kg$^{-1}$ of the target analytes. Results for scale, spine and soft fin ray are presented in FIG. 3. Taking into account the future applicability in aquaculture and wildlife, 0.1 g of every calcified structure was chosen for validation.

Figure 3:
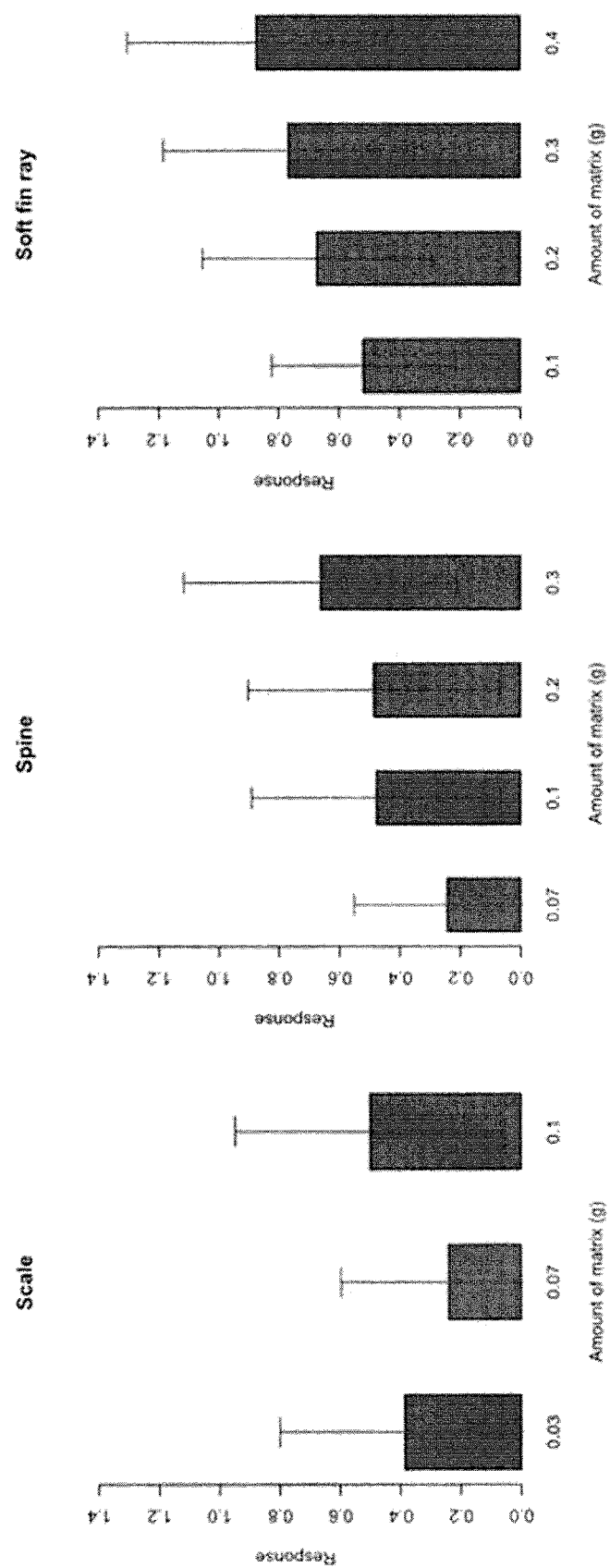
FIG. 3: Optimal amounts of matrix for scale, spine and soft fin ray for validation.

FIG. 3. Optimal Amounts of Matrix for Scale, Spine and Soft Fin Ray for Validation To remove mucus, known to contain endogenous,[65] as well as exogenous, glucocorticoids, intensive washing of all samples with ultrapure water was carried out.

Four solvents with different extraction efficiency were tested: methanol, 2-propanol, acetonitrile, and diethylether. Methanol gave the best results for the various glucocorticoids in scales as well as in spines and soft fin rays; in otoliths, no clear difference between solvents was seen (data not shown).

Next, time-dependence of incubation with methanol (15, 60, 120 minutes and 16 hours), as well as repeated extraction, was tested. For cortisol in fish scales, no improvement of extraction was seen after 60 minutes of incubation. No improvement of a second extraction was seen, nor of a combination of 15 minutes for 2 cycles (versus 1 cycle of 60 minutes). Results for scale, spine, and soft fin ray are presented in FIG. 4.

Figure 4:
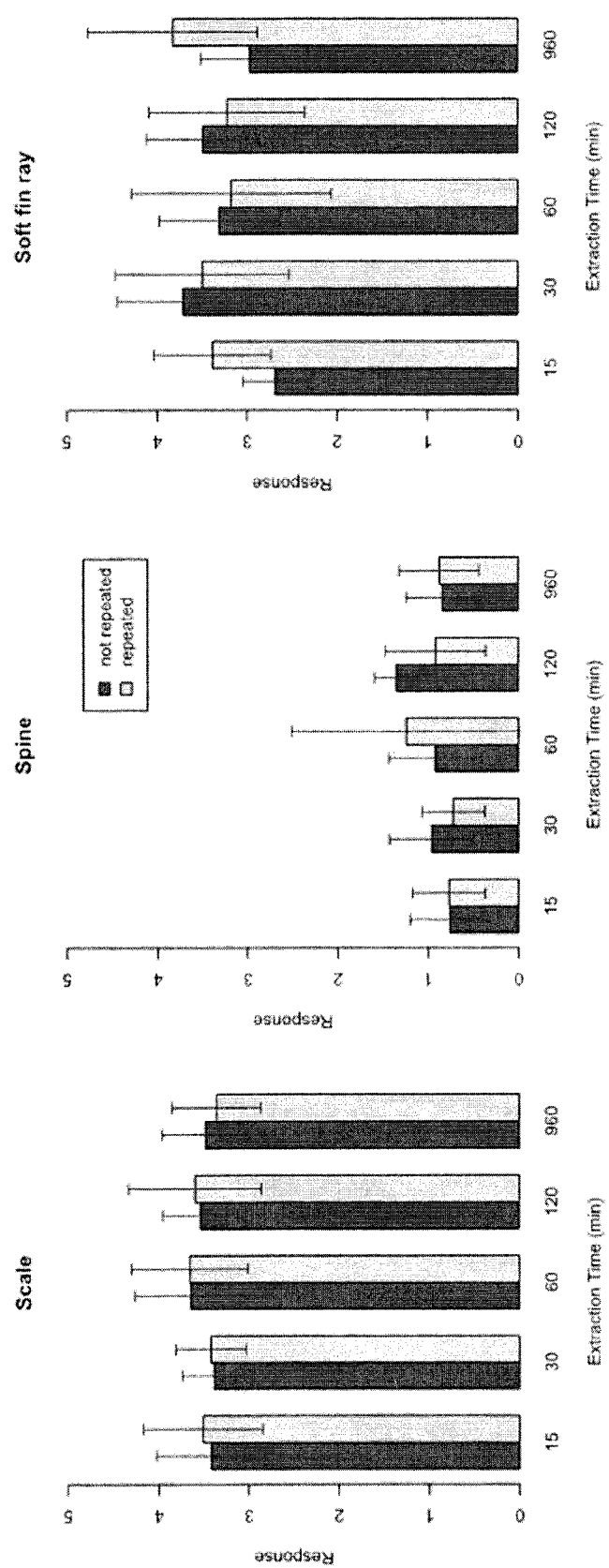
FIG. 4: Optimization of extraction time and repeats for cortisol in scale, spine and soft fin ray.

FIG. 4. Optimization of Extraction Time and Repeats for Cortisol in Scale, Spine and Soft Fin Ray As a high throughput and cost-effective method is needed, extraction in scales was standardized with 8 ml of methanol for 1 hour on an overhead shaker at room temperature.

SPE Procedure

C18 phase SPE cartridges were successfully used to extract glucocorticoids from biological samples such as plasma,[66] urine,[67] feces,[68] and, therefore, this column type was chosen to optimize the extraction and purification of the selected glucocorticoids from the calcified structures in this study.

Grace Pure™ SPE C18-Max (500 mg, 6 ml) columns are reversed phase sorbents with a polymerically bonded 17.1% carbon load on a silica-based support. The reversed phase extraction procedure was chosen since it binds moderately polar to non-polar compounds from a polar sample matrix. A bed size of 500 mg gives a sorbent retention capacity of 25 mg. Taking into account the predicted concentration range of glucocorticoids in scales as well as in the other calcified structures, this retention capacity will suffice to bind all analytes of interest. The conditioning, sample loading, washing, and elution steps for the SPE were optimized for solvent type and volume. The conditioning step with 3 ml of methanol to activate the sorbent ligands followed by 3 ml of ultrapure water to equilibrate the sorbent bed gave best results (average recovery of cortisol >90%). The minimal volume for both solvents was 2.5 ml, while tests using volumes over 3 ml did not improve purification. The sample loading step whereby the evaporated sample was resuspended in 5 ml $H_2O$/MeOH (80:20; v/v) gave the best results. Solvent combinations in which the proportion of ultrapure water and/or methanol were varied gave suboptimal results. Washing of the column with 4.5 ml $H_2O$/MeOH (65:35; v/v) gave the best results for glucocorticoid recovery. A higher concentration of methanol led to elution of glucocorticoids, while a lower concentration of methanol resulted in an increase of noise. The retained compounds were eluted with 2.5 ml $H_2O$/MeOH (20:80; v/v) into a 10 ml test tube. A lower elution volume or an increase of ultrapure water did not recover all glucocorticoids, while a higher elution volume or an increase of methanol was suboptimal regarding cost effectiveness and as it eluted more interfering compounds from the matrix, respectively. After evaporation, the sample was reconstituted in 100 µL $H_2O$/MeOH (80:20; v/v) in a vial and analyzed by means of LC-MS/MS. Reconstitution in 100 μt was chosen to have the possibility of a duplo injection. Solvent combinations in which the proportion ultrapure water to methanol were changed gave suboptimal results since the gradient for chromatographic analysis was optimized to start at $H_2O$/MeOH (80:20; v/v). Reconstitution in a concentration up to $H_2O$/MeOH (20:80; v/v) was possible but had negative effects on the chromatographic peak shapes.

Chromatographic Analysis

In a first step to optimize the chromatographic analysis using an AcQuity ULTRA PERFORMANCE LC® BEH C18 (1.7 μm; 2.1×100 mm) column, all compounds, as well as the internal standard, were tuned using the mass spectrometer in positive ($ESI^+$) and negative ($ESI^-$) electrospray ionization mode. Results obtained in $ESI^-$ gave small peaks but less noise, while $ESI^+$ gave overall better results and was chosen for further testing.

In a second step, different gradient systems using ultrapure water and nonpolar solvents like methanol and acetonitrile with 0.1% of formic acid were tested. At first, gradients using ultrapure water and acetonitrile were tested: a higher starting concentration of acetonitrile gave a shorter retention time and only separation of cortisol, cortisone and 17α-hydroxyprogesteron was seen; running a gradient increasing slowly the acetonitrile concentration resulted in loss of the 17α-hydroxyprogesteron peak, as well as a runtime of 12 minutes, making acetonitrile unsuitable as mobile phase. Subsequently, gradients using ultrapure water and methanol were tested: after running different gradients ranging from a slow to a very quick increase of the methanol concentration, all compounds were fully separated and variable concentrations of different additives were tested. The use of 0.5% acetic acid gave better results than 2 mM ammonium formiate at pH 3.0 or ammonium acetate at pH 5.0, but poorer than 0.1% formic acid. Subsequently, the concentration of formic acid was optimized and 0.1% formic acid was chosen; a lower concentration of formic acid resulted in unstable results due to the carryover from methods using other additives. Finally the column temperature and flow rate were optimized at 30° C. and 0.4 ml $minute^{-1}$, respectively, to have a total run time of 10 minutes.

In a last step, the MS/MS method was optimized: dwell times were increased for an optimal sensitivity to secure that the points across the peak for every ion of all compounds consisted of at least 20 data points and MS frame windows were optimized accordingly.

Validation

Concentration values of glucocorticoids in scales (or any other calcified structure) are not available in the published literature, which required the option for an initial working range from 1 μg $kg^{-1}$ to 50 μg $kg^{-1}$.

The apparent recovery for cortisol in fish scales below, at and above CCβ level ranged from 88.14% to 98.85%, all within the 80% to 110% performance criterion according to the requirements of the Commission Decision No. 2002/657/EC. Despite the fact that the homogenization of the pooled validation sample was not optimal (i.e., it was not a homogenous powder, but rather a pool of very fine fragments, the repeatability for cortisol in fish scales ranged from 12.36% to 17.15%. The intra-laboratory reproducibility ranged from 14.63% to 20.02%. The results for trueness, precision and measurement uncertainty for the analyzed compounds in fish scales are presented in Table 2.

TABLE 2

Values for trueness (apparent recovery AR, percent), coefficient of variation values (CV, percent) for precision (repeatability $CV_r$ and intra-laboratory reproducibility $CV_R$) and expanded measurement uncertainty (U, percent) for all compounds in fish scale

| Compound | Level (μg $kg^{-1}$) | AR (%) | $CV_r$ (%) | $CV_R$ (%) | $U^1$ (k = 2) (%) | $U^1$ (k = 3) (%) | $U^2$ (k = 2) (%) |
|---|---|---|---|---|---|---|---|
| Cortisol | 1 | 98.85 | 17.15 | 20.02 | 41.19 | 61.21 | 66.16 |
| | 5 | 88.14 | 12.36 | 15.01 | 41.88 | 56.89 | 58.08 |
| | 10 | 98.20 | 16.21 | 18.05 | 37.90 | 55.95 | 61.44 |
| | 25 | 90.97 | 13.81 | 14.85 | 38.73 | 53.58 | 56.08 |
| | 50 | 91.16 | 13.47 | 14.63 | 38.10 | 52.73 | 55.57 |
| Precursors | | | | | | | |
| 17α-Hydroxyprogesteron | 1 | 114.00 | 27.83 | 32.08 | 78.16 | 110.24 | 106.46 |
| | 5 | 104.44 | 33.09 | 43.74 | 91.92 | 135.66 | 131.31 |
| | 10 | 123.75 | 13.09 | 21.98 | 67.71 | 89.69 | 91.08 |
| | 25 | 135.64 | 6.64 | 16.23 | 68.10 | 84.33 | 96.06 |
| | 50 | 141.34 | 7.79 | 18.38 | 78.10 | 96.48 | 109.63 |
| 11-Deoxycortisol | 1 | —[3] | —[3] | —[3] | —[3] | —[3] | —[3] |
| | 5 | 68.53 | 20.09 | 26.44 | 84.35 | 110.79 | 96.79 |
| | 10 | 84.55 | 16.83 | 31.71 | 78.87 | 110.58 | 95.44 |
| | 25 | 102.42 | 8.59 | 15.37 | 33.16 | 48.53 | 56.19 |
| | 50 | 113.49 | 6.13 | 14.88 | 43.25 | 58.13 | 62.77 |
| Metabolites | | | | | | | |
| Cortisone | 1 | 104.37 | 38.94 | 66.90 | 138.17 | 205.07 | 196.46 |
| | 5 | 96.88 | 27.81 | 38.51 | 80.14 | 118.65 | 112.94 |
| | 10 | 93.67 | 24.26 | 37.06 | 80.45 | 117.51 | 108.22 |
| | 25 | 83.21 | 19.78 | 25.61 | 68.01 | 93.62 | 82.52 |
| | 50 | 84.28 | 17.20 | 18.91 | 53.54 | 72.45 | 68.23 |
| 20-Dihydrocortisone | 1 | 99.63 | 20.58 | 38.46 | 77.29 | 115.75 | 136.72 |
| | 5 | 102.05 | 18.72 | 37.38 | 76.81 | 114.19 | 119.88 |
| | 10 | 129.33 | 12.97 | 22.44 | 74.21 | 96.65 | 71.89 |
| | 25 | 138.74 | 12.35 | 18.61 | 75.96 | 94.57 | 73.71 |
| | 50 | 143.29 | 6.66 | 15.51 | 74.31 | 89.82 | 84.79 |

TABLE 2-continued

Values for trueness (apparent recovery AR, percent), coefficient of variation values (CV, percent) for precision (repeatability $CV_r$ and intra-laboratory reproducibility $CV_R$) and expanded measurement uncertainty (U, percent) for all compounds in fish scale

| Compound | Level ($\mu g\ kg^{-1}$) | AR (%) | $CV_r$ (%) | $CV_R$ (%) | $U^1$ (k = 2) (%) | $U^1$ (k = 3) (%) | $U^2$ (k = 2) (%) |
|---|---|---|---|---|---|---|---|
| Tetrahydrocortisol | 1 | 90.23 | 35.70 | 39.35 | 88.47 | 127.82 | 113.47 |
| | 5 | 95.97 | 31.72 | 30.10 | 64.23 | 94.33 | 90.78 |
| | 10 | 103.69 | 27.61 | 27.94 | 59.57 | 87.51 | 87.88 |
| | 25 | 104.04 | 25.11 | 24.42 | 52.88 | 77.30 | 78.88 |
| | 50 | 116.79 | 17.33 | 21.16 | 59.11 | 80.27 | 80.80 |
| Tetrahydrocortisone | 1 | 103.17 | 45.30 | 50.81 | 104.79 | 155.60 | 150.09 |
| | 5 | 108.83 | 26.85 | 37.09 | 83.01 | 120.10 | 116.11 |
| | 10 | 106.80 | 25.01 | 31.64 | 70.08 | 101.72 | 99.63 |
| | 25 | 103.61 | 24.83 | 34.06 | 71.73 | 105.79 | 104.19 |
| | 50 | 110.41 | 15.60 | 21.90 | 54.21 | 76.11 | 76.61 |

Figure 5:
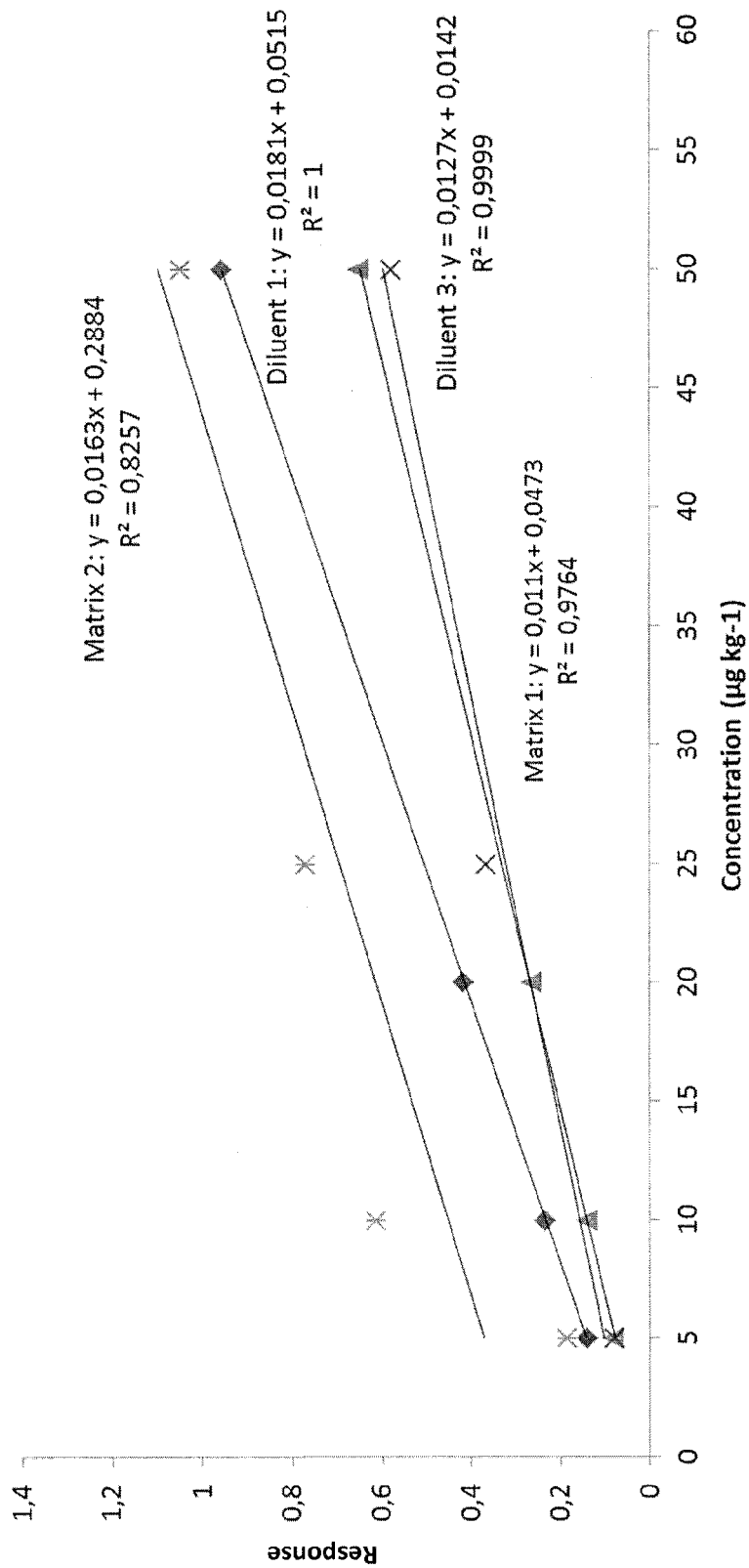
FIG. 5: Calibration curve in diluent and in matrix for cortisol in fish scales.
Figure 6B:
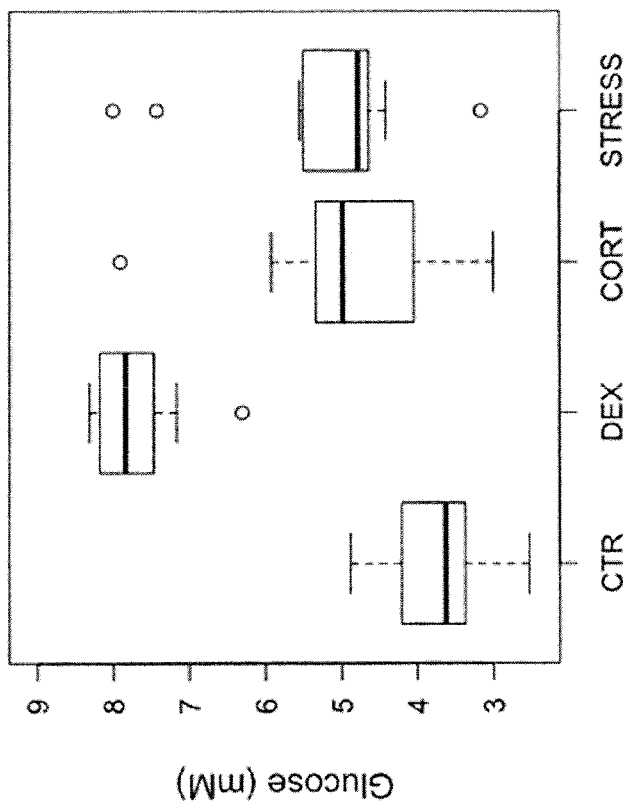
FIGS. 6A-6E: Plasma analyses of cortisol (nM) (FIG. 6A), glucose (mM) (FIG. 6B), lactate (mM) (FIG. 6C), total calcium (mM) (FIG. 6D), and osmolality (mOsmol kg$^{-1}$) (FIG. 6E) at day 42 of treatment. Fifty percent of the observations occurs between the lower and upper edges of the box (the first and third quartiles) and the whiskers extend to the most extreme observation, which is no more than 1.5 times the interquartile range from the box; open circles represent values outside the range mentioned.
Figure 6A:
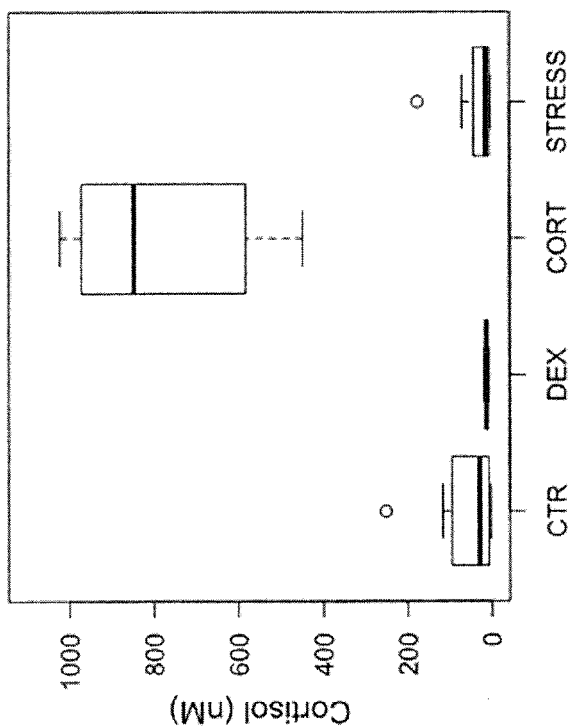
Figure 6D:
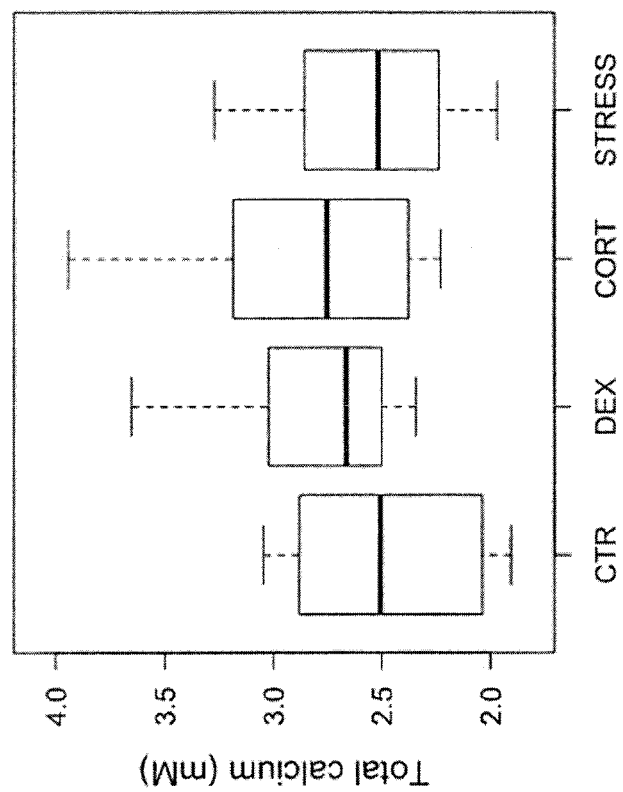
Figure 6C:
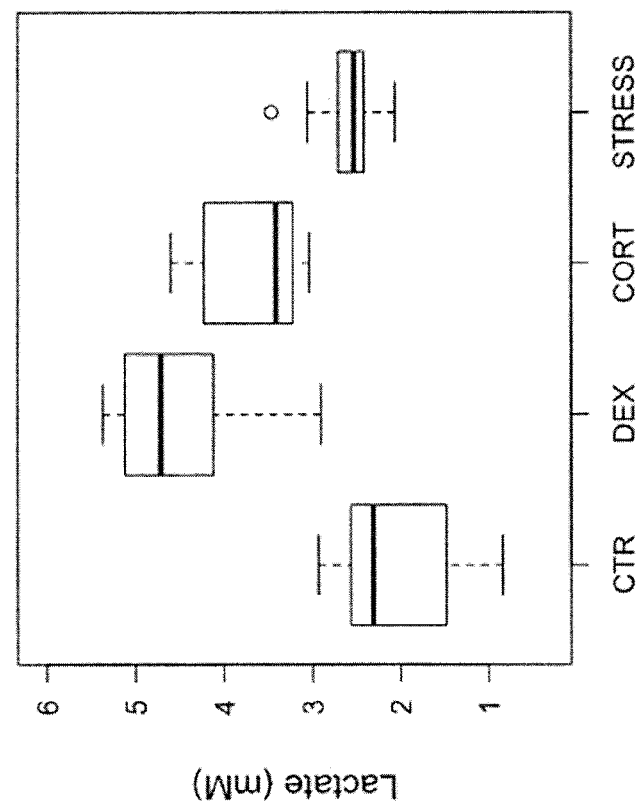
Figure 6E:
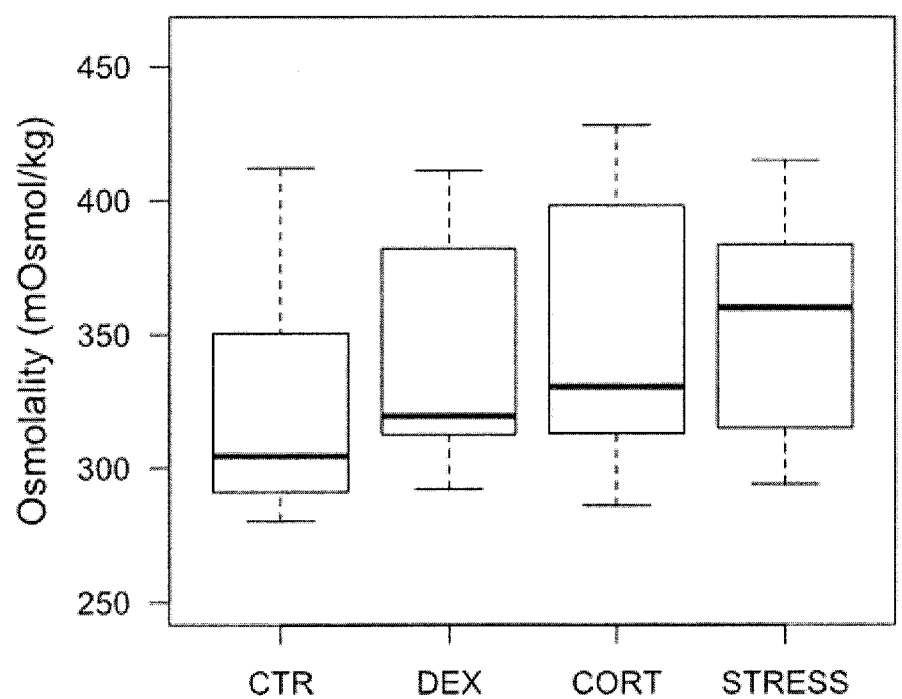

[1] Calculation of the expanded measurement uncertainty using linear summation with a coverage factor (k) of 2 (95% confidentiality interval), respectively, of 3 (99% confidentiality interval)
[2] Calculation of the expanded measurement uncertainty using quadratic summation (Nordtest method) with a coverage factor (k) of 2 (95% confidentiality interval)
[3] Insufficient response for the qualifier ion Since in future research matrix-matched calibration curves are not practically feasible, possible matrix effects were determined by comparing data from calibration curves in diluent to matrix-matched ones in the range from 5 μg kg$^{-1}$ to 50 μg kg$^{-1}$ for all compounds in every calcified structure. FIG. 5 indicates no significant effect for cortisol in fish scales (taking into account the biological variation of the sample) but as calibration curves in diluent and matrix are normally divided, quantification using calibration curves in diluent is possible.

FIG. 5. Calibration Curve in Diluent and in Matrix for Cortisol in Fish Scales

Subsequently, the linearity of the response for all the compounds in every calcified structure was tested using four-fold calibration curves in diluent consisting out of five calibration points, ranging from 5 μg kg$^{-1}$ to 100 μg kg$^{-1}$, analyzed under intra-laboratory reproducibility conditions. When assessing the linearity in this range for all compounds, no coefficient of determination ($R^2$) values lower than 0.99 were found. Furthermore, the calculated model indicated normal distribution for all compounds. The results for linearity, CCα, and CCβ, for all compounds in a fish scale are presented in Table 3.

TABLE 3

Coefficient of determination ($R^2$) of calibration curves and values of the decision limit (CCα, μg kg$^{-1}$) and detection capability (CCβ, μg kg$^{-1}$) for all compounds in fish scales

| Compound | $R^2$ | CCα (μg kg$^{-1}$) | CCβ (μg kg$^{-1}$) |
|---|---|---|---|
| Cortisol | 0.999 | 2.74 | 4.64 |
| Precursors of cortisol | | | |
| 17α-Hydroxyprogesteeron | 0.998 | 2.37 | 3.90 |
| 11-Deoxycortisol | 0.997 | 1.79 | 2.88 |
| Metabolites of cortisol | | | |
| Cortisone | 0.996 | 3.74 | 6.36 |
| 20-Dihydrocortisone | 0.998 | 2.43 | 4.07 |
| Tetrahydrocortisol | 0.997 | 4.84 | 8.25 |
| Tetrahydrocortisone | 0.992 | 0.99 | 1.68 |

Sensitivity of the method was determined by making a dilution series on blank matrix samples resulting in a method with good sensitivity for all compounds in fish scales when taking into account the predicted working range. Selectivity of the method was proven by analyzing blank and spiked samples. In spiked samples, all compounds appeared at predicted retention times with their two ion transitions. The ion ratios were compared with the standard injection and were found acceptable according to the requirements of the Commission Decision No. 2002/657/EC. Furthermore, no interfering peaks were observed.

The robustness of the method was tested during method development for all critical steps like extraction and SPE purification by varying the optimal value.

A UPLC-MS/MS method for cortisol, its precursors (17α-hydroxyprogesterone and 11-deoxycortisol), cortisone and metabolites (tetrahydrocortisol and tetrahydrocortisone) in fish scales was developed in an EN ISO/IEC 17025:2005 accredited environment and validated according to the requirements of the Commission Decision No. 2002/657/EC and was proven to be suitable for its intended purposes. In addition, the method was tested and validated for three other calcified structures being spine, soft fin ray and otolith.

Example 2

Quantification of Glucocorticoid Levels in Scales of Stressed vs Unstressed Seabass (*Dicentrarchus labrax*)

Method and Materials (see Example 1)
Experimental Set-up

The trial existed out of two replicates of three conditions: control (low stress, medium stress and high stress). Stress was a combination of various types of stressors (crowding, chasing and air exposure) randomly administered during a period of 3 weeks. At several unpredictable moments a day, stressors were administered as indicated:

low stress: confinement (25% volume), 30 minutes every 2nd day medium stress: confinement (25% volume), 30 minutes, chasing 5 minutes every 2nd day high stress: confinement (10% volume), 30 minutes, chasing 5 minutes every 2nd day, air exposure 1 minute once per week Plasma cortisol was measured in duplicate using an RIA in a 96-well plate according to Gorissen et al.[69]. The primary antibody shows a 100% cross-reactivity with cortisol, 0.9% with 11-deoxycortisol, 0.6% with corticosterone, and <0.01% with 11-deoxycorticosterone, progesterone, 17-hydroxyprogesterone, testosterone and estradiol. All wells except the "non-specifics" received 100 μl cortisol antibody (Cortisol Antibody[xm210] monoclonal and IgG purified (Abeam); 1:2000 in 50 mM NaHCO3, 50 mM NaH2CO3, 0.02% NaN3, pH=9.6) and were incubated overnight at 4° C. The following day, the plates were washed three times with 200 μl/well wash buffer (100 mM Tris, 0.9% NaCl, 0.02% NaN3). Subsequently, non-specific sites were blocked by the addition of 100 μblocking buffer (100 mM Tris, 0.9% NaCl, 0.02% NaN3, 0.25% Normal Calf Serum) to each well. Plates were covered and incubated for one hour at 37° C. Subsequently, 10 μl of standard (4 pg-2048 pg cortisol/10 μl assay buffer containing 100 mM Tris, 0.9% NaCl, 0.1% 8-anilino-1-naphthalenesulfonic acid, 0.02% NaN3) or 10 μl of undiluted plasma or perifusion medium was added to designated wells. Non-specifics and B0 received 10 μl assay buffer. After the addition of standards and samples, 90 μl (333 Bq) of $3_H$-hydrocortisone (PerkinElmer. USA, 1:10,000 in assay buffer) solution was added to all wells. Plates were incubated for four hours at room temperature, or stored overnight at 4° C. The plates were then washed three times with wash buffer. After the final wash step, all wells received 200 μl of OPTIPHASE HISAFEO-3 scintillation liquid (PerkinElmer, USA) and were covered. Beta-emission was quantified by a 3-minute count per well using a MICROBETA PLUS™ (Wallac/PerkinElmer, USA). Inter- and intra-assay variations were 12.5 and 3.5%, respectively.

Results

| CORTISOL IN PLASMA | Mean cortisol concentration (ng/ml) in plasma | Standard deviation (ng/ml) | Variation coefficient (%) |
|---|---|---|---|
| Low stress | | | |
| Replicate 1 | 274.81 | 151.81 | 55.24 |
| Replicate 2 | 100.86 | 101.70 | 100.84 |
| All replicates (20 samples) | 183.26 | 152.90 | 83.43 |
| Medium stress | | | |
| Replicate 1 | 319.00 | 106.04 | 33.24 |
| Replicate 2 | 190.58 | 136.65 | 71.70 |
| All replicates (20 samples) | 254.79 | 136.06 | 53.40 |
| High stress | | | |
| Replicate 1 | 112.64 | 95.22 | 84.53 |
| Replicate 2 | 187.92 | 73.90 | 39.32 |
| All replicates (20 samples) | 150.28 | 91.50 | 60.89 |

| CORTISOL IN SCALE | Mean cortisol concentration (μg kg$^{-1}$) in scale | Standard deviation (μg kg$^{-1}$) | Variation coefficient (%) |
|---|---|---|---|
| Low stress | | | |
| Replicate 1 | 1.90 | 1.00 | 53.58 |
| Replicate 2 | 1.50 | 1.70 | 109.19 |
| All replicates (20 samples) | 1.70 | 1.35 | 79.58 |
| Medium stress | | | |
| Replicate 1 | 2.40 | 2.00 | 83.29 |
| Replicate 2 | 2.10 | 1.50 | 69.13 |
| All replicates | 2.27 | 1.72 | 75.86 |
| High stress | | | |
| Replicate 1 | 3.20 | 2.30 | 69.57 |
| Replicate 2 | 3.60 | 4.00 | 109.08 |
| All replicates (20 samples) | 3.44 | 3.15 | 91.50 |

Example 3

Quantification of Glucocorticoid Levels in Scales of Carp (Cyprinus carpio L.)

Method and Materials (See Also Example 1 and Further) Experimental Set-up

The trial with carp exists out of two replicates of four conditions, each with six fish: control (unstressed), dexamethasone (inhibition of stress pathway), cortisol (activation of stress pathway) and stress induced by various stressors given in an ad random administered manner for 6 weeks.

Methods

Experimental procedures were according to Dutch legislation and approved by the local ethical committee. Common carp (Cyprinus carpio L.) were reared at the Radboud University of Nijmegen to ensure the history. Growing adult fish (at day 21: 340±92 g and 24.6±2.4 cm; at day 42: 377±108 g and 25.4±2.5 cm), held under 12:12 hours light:dark, fed two meals a day (09:30 am and 15:30 pm) at 0.9% of body weight were kept at 20.0±0.4° C. for 6 weeks. Four groups, with two tank replicates per group, of six fish per 140-L tank each, were set up. Fish of the CTR group were left undisturbed. The DEX and CORT groups received feed spiked at 500 mg kg$^{-1}$. The STRESS group was stressed once daily; type, duration and timing of stressors were applied randomly and included: netting (15-60 minutes), air exposure (1-3 minutes), temperature drop (up to 5° C.), chasing (up to 10 minutes) and confinement (in a bucket with low water level). During the entire experiment, no indications of impaired health and behavior were noticed. After 42 days, fish were anesthetized in 2-phenoxy-ethanol (0.1% v/v) and sacrificed, blood taken from the caudal vessels and scales (ontogenetic and the 21-day regenerated scales) collected. Plasma was analyzed for cortisol,[69] glucose,[70] lactate,[70] total calcium,[71] and osmolality.[70] Scales were sampled from a standardized row dorsally to the lateral line. MNE of target genes was assessed using eeflal rps5 and beta-actin as reference genes[72]. All parameters were modeled using a linear mixed model in SAS 9.4 (SAS Institute Inc., Cary, N.C.) with treatment, day of sampling and their interaction (where appropriate) as fixed effects. A random intercept for tank was introduced in the model to correct for clustering of fishes in tanks. Dunnett's test was performed to compare treatments with controls.

Results

1) Controlling the Rationale and Execution of the Experimental Set-Up

During a 6-weeks trial, undisturbed (CTR) and daily stressed (STRESS) carp were compared. Dexamethasone (DEX) or cortisol (CORT) fed fish served as negative and positive controls for cortisol incorporation in the scale, respectively. In all treatments, the feed ration provided was consumed within 5 minutes, all fish remained clinically healthy as indicated by the condition factor[73] and no mortality was observed. Adequate water quality was maintained by daily (pH, temperature, dissolved oxygen) or weekly (nitrite, nitrate, ammonium) monitoring. A contribution of waterborne glucocorticoids, as a result of leakage from feed, to the effects observed, can be excluded. Analyses of cortisol, its precursors and metabolites by in-house developed and validated (see scale cortisol) ultra-performance liquid chromatography tandem mass spectrometry (UPLC-MS/MS) revealed that elevated cortisol concentrations in water returned to baseline within 2.5 hours after feeding.

Results for five blood parameters commonly used as stress indicators confirm that DEX fish may be considered as negative, and CORT fish as positive controls, respectively (FIGS. 6A-6E). Plasma cortisol had elevated in the CORT group (CORT vs. CTR: P<0.0001), confirming the absorption of cortisol from feed into the blood; in STRESS fish, cortisol levels did not differ from negative controls indicating the unsuitability of the latter for chronic stress assessment. The secondary stress parameter plasma glucose, reflecting predicted glucocorticoid actions (gluconeogenesis), had increased in DEX (DEX vs. CTR: P<0.0001), while CORT (CORT vs. CTR: P=0.2004) and STRESS (STRESS vs. CTR: P=0.0531) did not differ significantly, in line with the more potent action of DEX. Plasma lactate had increased in DEX (DEX vs. CTR: P<0.0001) and CORT (CORT vs. CTR: P=0.0004), but not significantly in STRESS (STRESS vs. CTR: P=0.4224) in line with the downstream effects of DEX and CORT. Plasma total calcium and osmolality were not affected, indicating that the treatments did not exceed the resilience of the fish and did not evoke distress. It was concluded that (i) CTR, DEX and CORT treatments elicited the intended glucocorticoid actions; (ii) in plasma of STRESS fish, no signs of activation of HPI axis were observed; (iii) plasma parameters are poor predictors for chronic stress as they reflect no more than a snap-shot of the stress response at a given moment.

Figure 7:
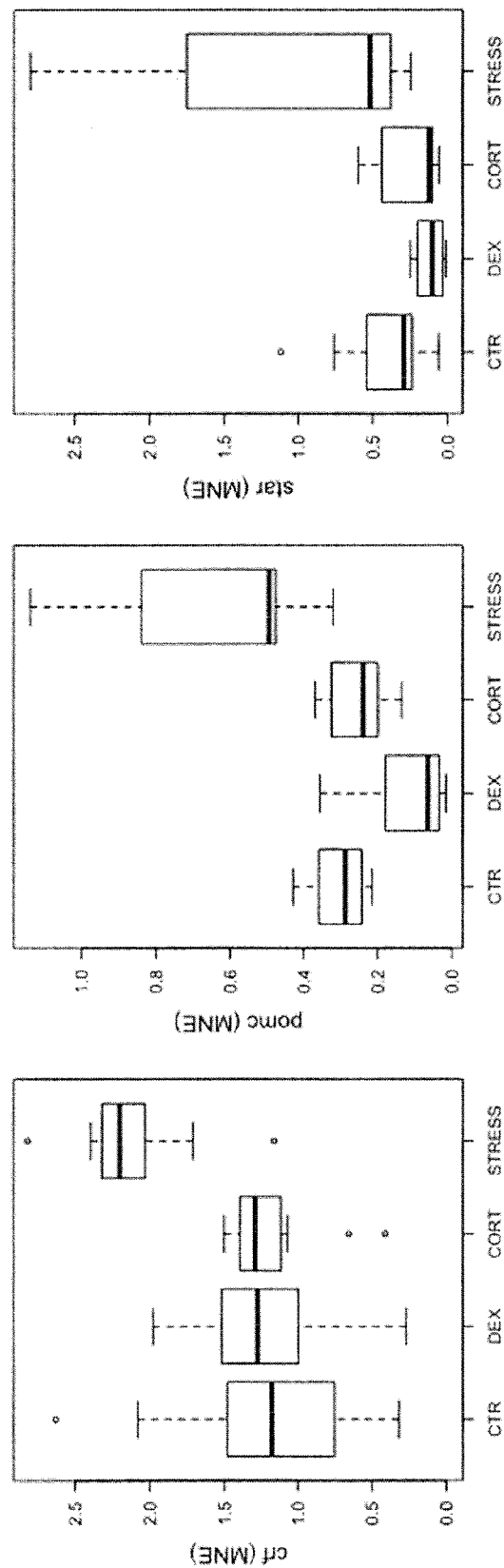
FIG. 7: Analyses of hypothalamic (crf), pituitary pars distalis (pomc), and interrenal (star) genes (Mean Normalized Expression—MNE) at day 42 of treatment. The whiskers in boxplots are defined as in FIGS. 6A-6E.

From the above, it follows that plasma cortisol values in chronically stressed fish do not provide an adequate read-out for stress experienced. However, FIG. 7 shows that the endocrine stress axis is most certainly activated. The expression of hypothalamic, pituitary pars distalis, and interrenal key genes crf (STRESS vs. CTR: P=0.0002), pomc (STRESS vs. CTR: P<0.0001), and star (STRESS vs. CTR: P=0.0140), respectively, are significantly up-regulated indeed. Negative glucocorticoid feedback is indicated by significantly decreased pomc expression (DEX vs. CTR: P=0.0236).

Figure 8:
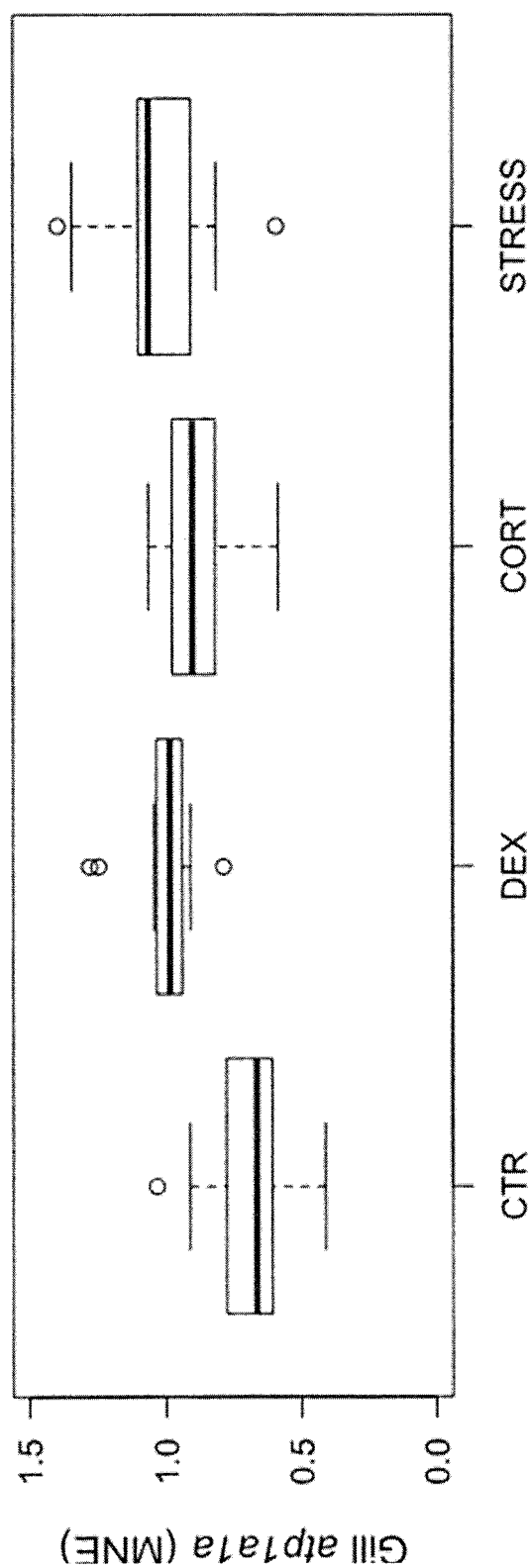
FIG. 8: Gene expression of atp1a1a in gills (MNE) after 42 days of treatment. The whiskers in boxplots are defined as in FIGS. 6A-6E.

A second line of evidence for chronic stress, not visible at the level of plasma cortisol, is the up-regulation of the gene encoding the subunit α1 of the branchial Na$^+$/K$^+$-ATPase[74] (FIG. 8). In DEX (DEX vs. CTR: P=0.0001), CORT (CORT vs. CTR: P<0.0001) and STRESS (STRESS vs. CTR: P=0.0215) fish, significantly enhanced expression levels were found, indicative of corticoid action.

In summary, results indicate that fish of the STRESS group were chronically stressed. Next, quantification of cortisol in the elasmoid scale was researched.

2) Cortisol in Ontogenetic Scales of Fish as Biomarker for Chronic Stress

Figure 9:
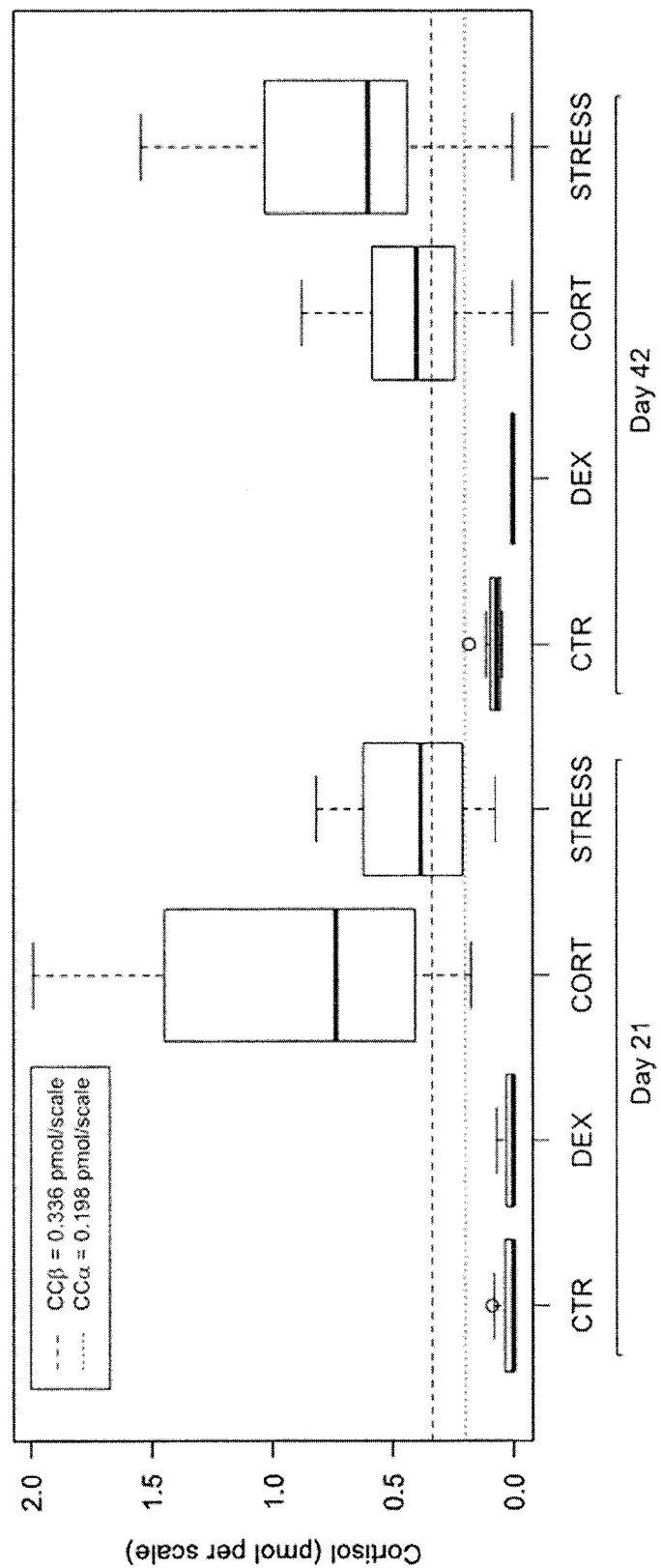
FIG. 9: Cortisol (pmol per scale) in ontogenetic scales after 21 and 42 days of treatment (CCα=decision limit and CCβ=detection capability). One value (2.8 pmol per scale) of STRESS day 42 was omitted in the boxplot for reasons of presentation. The whiskers in boxplots are defined as in FIGS. 6A-6E.

Five (day 21) to six (day 42) scales were analyzed for cortisol with a validated UPLC-MS/MS method (according to the requirements of the Commission Decision No. 2002/657/EC) in an NBN EN ISO/IEC 17025 regulated environment. All CTR and DEX fish showed scale cortisol values below the detection capability (CCβ); 10 out of 12 CORT fish at day 21 showed values above CCβ and all were above CCβ at day 42; 7 out of 11 STRESS fish at day 21 showed values above CCβ and all were above CCβ at day 42 (FIG. 9). Upon comparing treatments, at day 21, a significant accumulation was found for CORT fish (CORT vs. CTR: P<0.0001); at day 42 a significant accumulation was found for STRESS fish (STRESS vs. CTR: P=0.0001). When comparing within treatments from 21 to 42 days, a significant increase in scale cortisol was found in STRESS (P=0.0031) and CORT (P=0.0026) fish, respectively. These findings are in line with the predicted incorporation and accumulation of cortisol in scales over time and validate the scale cortisol content as a biomarker for chronic stress. In line with the predicted effect of blocking endogenous cortisol production by DEX, no cortisol incorporation in scales of DEX-treated fish was found. On the other hand, feeding cortisol and physically stressing the fish enhanced scale cortisol levels.

In summary, the results for cortisol in ontogenetic scales confirm that cortisol in scales reflect the stress level experienced by fish over time. Quantification of cortisol in the regenerating scale as additional tool for chronic stress quantification and its correlation to the gene expression level of the most abundant matrix protein collagen 1α was researched.

3) Next to Ontogenetic Scales, Cortisol also Accumulates in Regenerating Scales

Figure 10:
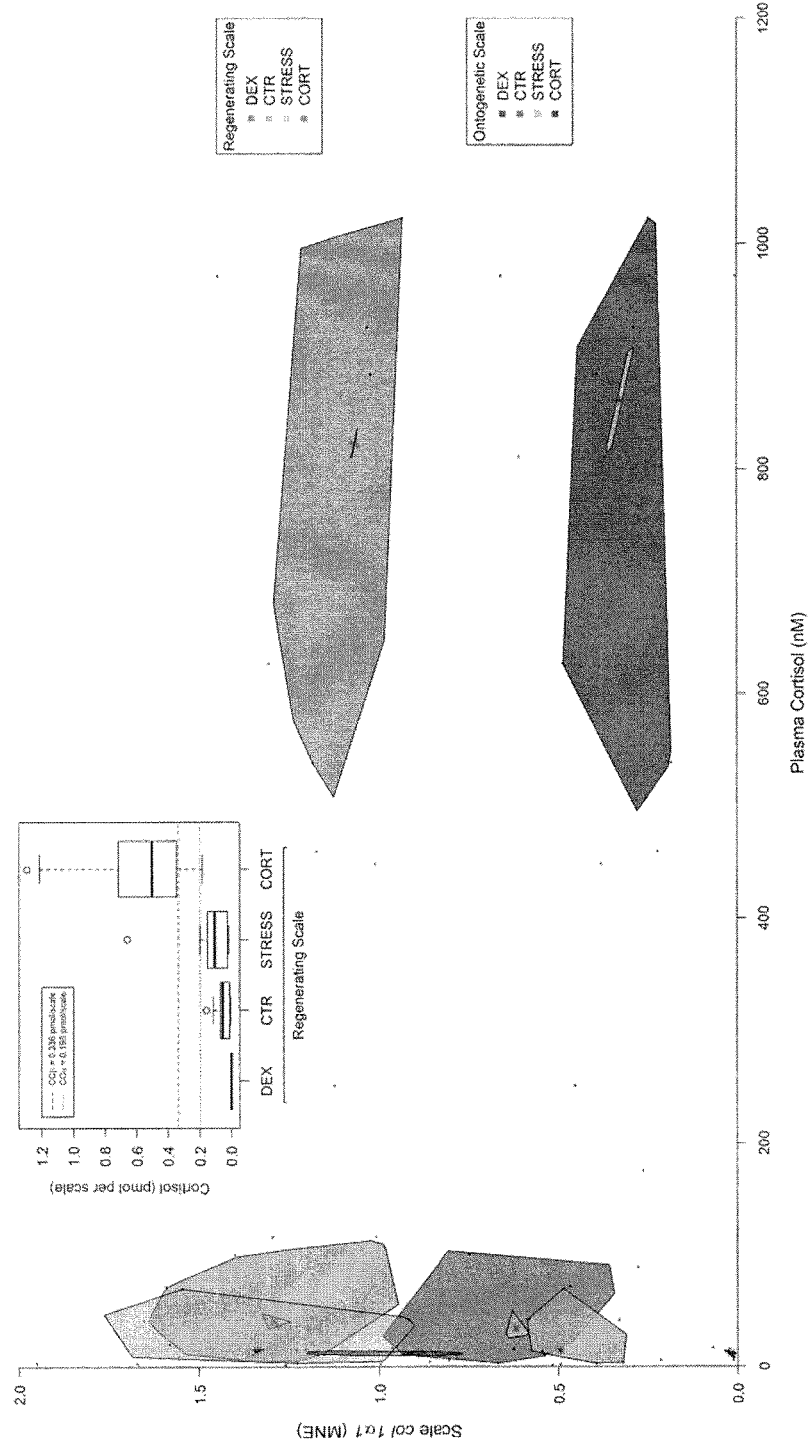
FIG. 10: Bagplot of relative colla1 expression of ontogenetic and regenerating scales (MNE) versus plasma cortisol (nM). The bag contains 50 percent of all observations. The inset shows cortisol (pmol per scale) in regenerating scales of 21 days. The whiskers in boxplots are defined as in FIGS. 6A-6E.

Cortisol concentrations were determined in five regenerated scales per fish 21 days after removal of the ontogenetic scale (FIG. 10). The MNE of colla1 was found to be inhibited in ontogenetic scales and correlates with high plasma cortisol level, in line with the well-known inhibitory effects of glucocorticoids on bone formation. In regenerating scales, the scleroblasts (scale-forming osteoblast-like cells[75]) appear insensitive to glucocorticoid feedback as shown by similar colla1 expression in all treatments. Morphologically, regenerated scales of CTR, STRESS, and CORT were found to be similar, while the area, perimeter and number of ridges of scales of DEX fish showed significantly lower values indicative of disturbed and retarded regeneration. The high cortisol plasma level in CORT fish at the moment of sampling of regenerating and ontogenetic scales at day 42 correlates with a high scale cortisol content, and this confirms that free cortisol incorporates in scales. Furthermore, regenerating scale cortisol content in STRESS fish appeared to be as yet not significantly higher than that of CTR but lower than CORT, indicating that the maximal sequestering of cortisol in the matrix had not been reached. Hereby, the extremely low amount of matrix analyzed (average of 4 mg of scale) should be noticed. A significant increase in scale cortisol in CORT fish (CORT vs. CTR: P<0.0001) was observed. This finding is in line with the incorporation and accumulation of cortisol in scales over time with higher plasma cortisol levels available, hereby reconfirming the findings on ontogenetic scales. The results for regenerating scales corroborate the results for ontogenetic scales and, thus, the fact that cortisol in scales reflects the stress level experienced by fish in time.

Example 4

Quantification of Glucocorticoid Levels in Scales of Tilapia (*Oreochromis mossambicus*)

Method and Materials (see Example 1 and Further) Experimental Set-up

The trial with tilapia exists out of two replicates of four conditions, each with six fish: control (unstressed), dexamethasone (inhibition of stress pathway), cortisol (activation of stress pathway) and stress induced by various stressors given in an ad random administered manner for 6 weeks.

Methods

Experimental procedures were according to Dutch legislation and approved by the Animal Ethics Committee of the Radboud University (permit number: RU-DEC2013-192). Tilapia (*Oreochromis mossambicus*) were reared at the Radboud University of Nijmegen to ensure the history. Growing adult fish (at day 21: 321±37 g and 26.0±0.9 cm; at day 42: 328±38 g and 26.5±0.9 cm), held under 12:12 hours light:dark, fed two meals a day (09:30 am and 15:30 pm) at 0.9% of body weight were kept at 20.0±0.4° C. for 6 weeks. Two groups, with two tank replicates per group, of six fish per 140-L tank each, were set up. Fish of the CTR group were left undisturbed. The STRESS group was stressed once daily; type, duration and timing of stressors were applied randomly and included: netting (15-60 minutes), air exposure (1-3 minutes), temperature drop (up to 5° C.), chasing (up to 10 minutes) and confinement (in a bucket with low water level). During the entire experiment, no indications of impaired health and behavior were noticed. After 42 days, fish were anesthetized in 2-phenoxy-ethanol (0.1% v/v) and sacrificed, blood taken from the caudal vessels and scales (ontogenetic and the 21-day regenerated scales) collected. Plasma was analyzed for cortisol, glucose,[70] total calcium,[71] and osmolality.[70] Scales were sampled from a standardized row dorsally to the lateral line and analyzed using ultra-performance liquid chromatography tandem mass spectrometry (UPLC-MS/MS).

Results

Controlling the Rationale and Execution of the Experimental Set-up

During a 6-week trial, undisturbed (CTR) and daily stressed (STRESS) tilapia were compared. In all treatments, the feed ration provided was consumed within 5 minutes, all fish remained clinically healthy as indicated by the condition factor[73] and no mortality was observed. Adequate water quality was maintained by daily (pH, temperature, dissolved oxygen) or weekly (nitrite, nitrate, ammonium) monitoring. A contribution of waterborne glucocorticoids, as a result of leakage from feed, to the effects observed, can be excluded. Analyses of cortisol, its precursors and metabolites by in-house developed and validated UPLC-MS/MS revealed that elevated cortisol concentrations in water returned to baseline within 2.5 hours after feeding.

Figure 11:
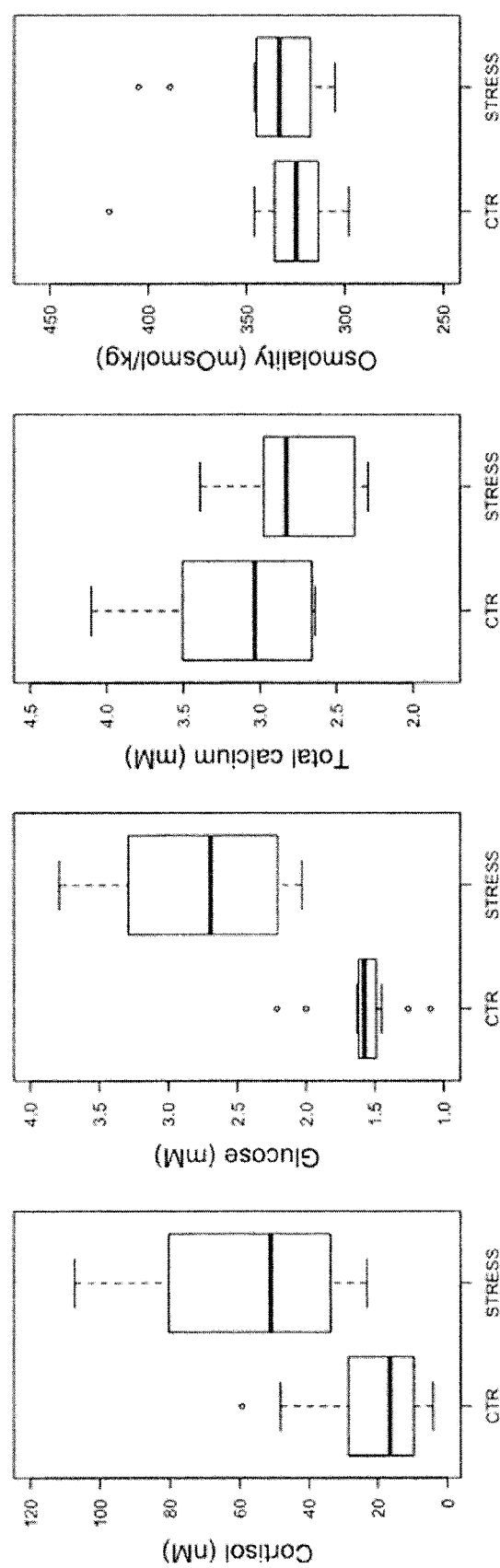
FIG. 11: Plasma analyses of cortisol (nM), glucose (mM), total calcium (mM), and osmolality (mOsmol kg$^{-1}$) at day 42 of treatment. Fifty percent of the observations occurs between the lower and upper edges of the box (the first and third quartiles) and the whiskers extend to the most extreme observation, which is no more than 1.5 times the interquartile range from the box; open circles represent values outside the range mentioned.

Four blood parameters commonly used as stress indicators were analyzed (FIG. 11). Plasma cortisol had elevated in the STRESS group (STRESS vs. CTR: P=0.0014), indicating the suitability of the latter for acute stress assessment. The secondary stress parameter plasma glucose, reflecting predicted glucocorticoid actions (gluconeogenesis), had increased in STRESS (STRESS vs. CTR: P=0.0006) and differed significantly. Plasma total calcium and osmolality were not affected, indicating that the treatments did not exceed the resilience of the fish and did not evoke distress. It was concluded that (i) STRESS treatment elicited the intended glucocorticoid actions as in plasma of STRESS fish where signs of activation of HPI-axis were observed; and (ii) plasma parameters are poor predictors for chronic stress as they reflect no more than a snap-shot of the stress response at a given moment.

Cortisol in Ontogenetic Scales of Fish as Biomarker for Chronic Stress

Five (day 21) to six (day 42) scales were analyzed for cortisol with a validated UPLC-MS/MS method (according to the requirements of the Commission Decision No. 2002/657/EC (EC, 2002) in an NBN EN ISO/IEC 17025 (EN ISO/IEC, 2005) regulated environment.

Figure 12:
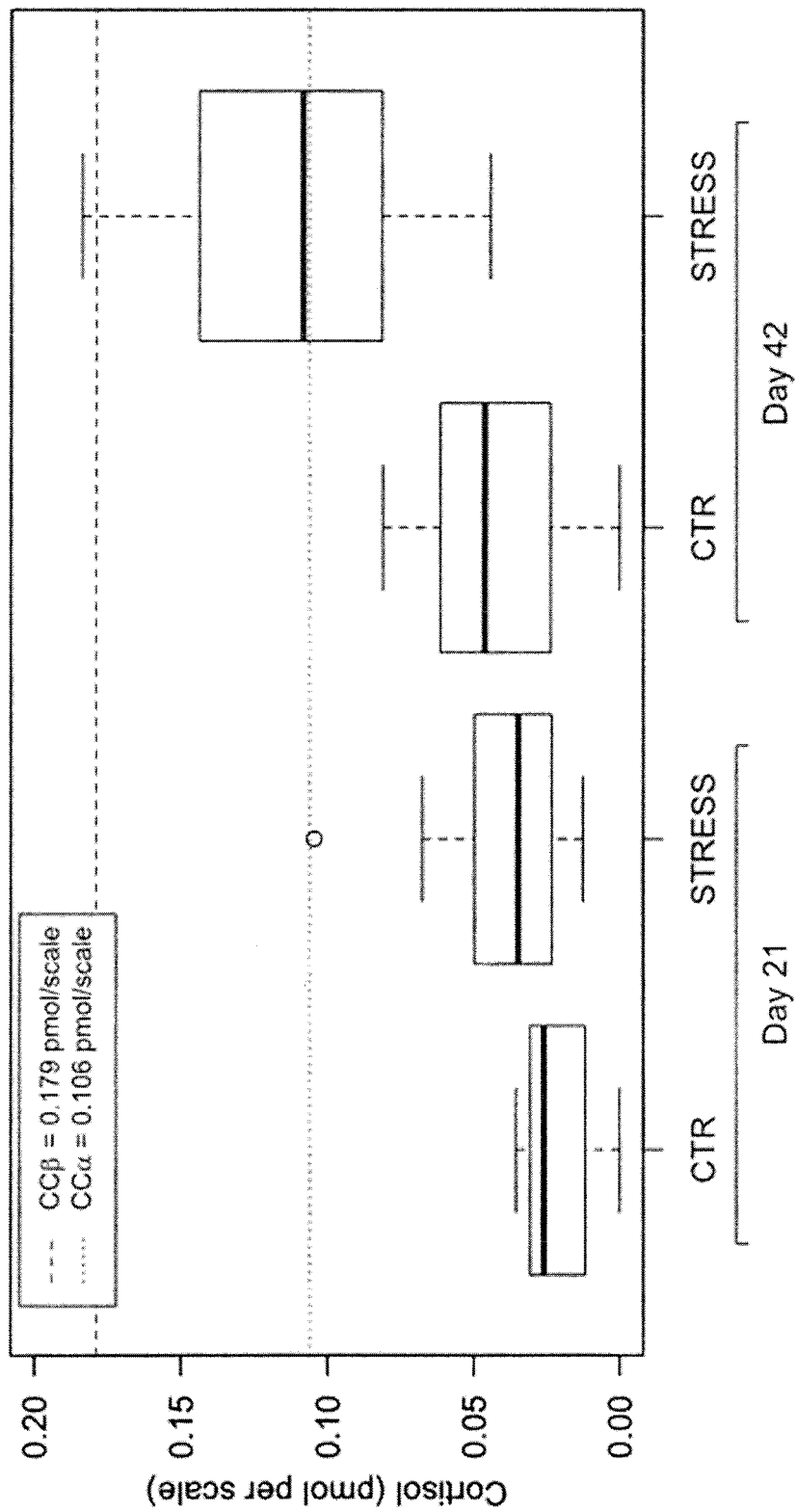
FIG. 12: Cortisol (pmol per scale) in ontogenetic scales after 21 and 42 days of treatment (CCα=decision limit and CCβ=detection capability). The whiskers in boxplots are defined as in FIG. 11.

At day 21, all CTR and STRESS fish showed scale cortisol values below the decision limit (CCα), while at day 42, levels of STRESS fish were mostly above CCα (FIG. 12).

Upon comparing treatments, at day 21, a near significant accumulation was found for STRESS fish (STRESS vs. CTR: P=0.0590); at day 42, a near significant accumulation was found for STRESS fish (STRESS vs. CTR: P=0.0515). When comparing within treatments from 21 to 42 days, no significant increase in scale cortisol was found in CTR (P=0.3962), while a significant increase in scale cortisol was found in STRESS (P=0.0020) fish. These findings are in line with the predicted incorporation and accumulation of cortisol in scales over time and further validate the scale cortisol content as a biomarker for chronic stress. In line with the predicted effect in the control group, no significant cortisol incorporation in scales of CTR fish (CTR21 vs. CTR42: P=0.0770) was found. On the other hand, physically stressing the fish enhanced scale cortisol levels (STRESS21 vs. STRESS42: P<0.0001).

In summary, the results for cortisol in ontogenetic scales confirmed the initial findings in carp that cortisol in scales reflect the stress level experienced by fish over time. Next, quantification of cortisol in the regenerating scale as an additional tool for chronic stress quantification was researched.

Next to Ontogenetic Scales, Cortisol also Accumulates in Regenerating Scales

Figure 13:
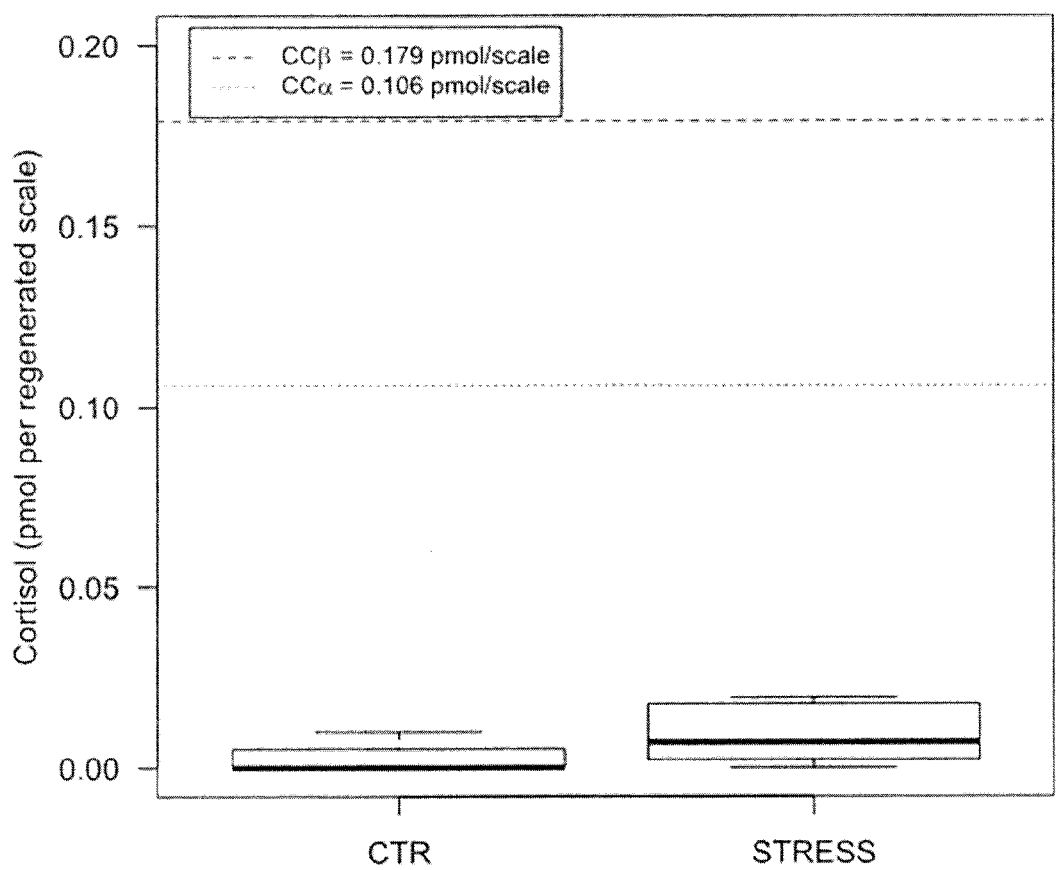
FIG. 13: Cortisol (pmol per scale) in regenerating scales of 21 days of treatment (CCα=decision limit and CCβ=detection capability). The whiskers in boxplots are defined as in FIG. 11.

Cortisol concentrations were determined in five regenerated scales per fish 21 days after removal of the ontogenetic scale (FIG. 13).

A significant increase in regenerating scale cortisol in STRESS fish (STRESS vs. CTR: P=0.0105) was observed. The high cortisol plasma level in STRESS fish at the moment of sampling of regenerating and ontogenetic scales at day 42 correlates with a high scale cortisol content, and this confirms the hypothesis that free cortisol incorporates in scales. This finding is in line with the predicted incorporation and accumulation of cortisol in scales over time with higher plasma cortisol levels available, hereby reconfirming the findings on ontogenetic scales. The results for regenerating scales corroborate the results for ontogenetic scales as well as the previous findings on carp and thus confirm that cortisol in scales reflects the stress level experienced by fish in time.

The assay of cortisol in plasma, as well as in alternative matrices such as feces, mucus and water, is not suitable for assessment of chronic stress. It was shown that the scale cortisol content is highly suitable for quantification of chronic stress in fish; this notion made scale cortisol an innovative and beyond state-of-the art biomarker with high potential impact in science and industries related to fish (e.g., physiology, toxicology, immunology, behavioral studies, etc.). The findings presented for carp and for tilapia are applicable for all fish with elasmoid scales (e.g., carp). In a broader sense, placoid (e.g., shark) and ganoid (e.g., sturgeon) scales are suitable as well, expanding the use of this biomarker to other actinopterygian and even chondrichtyan species. Finally, this new tool for chronic stress monitoring has a huge valorization potential to be adopted in a broad range of governmental, academic and industrial settings such as decision making on animal-friendly aquaculture (e.g., animal-based optimization of Recirculating Aquaculture Systems and improvement of product quality), monitoring of wild fish stocks (e.g., ecology-based population dynamics), the welfare of fish in public aquaria and in animal trials. The development of a financially, logistically and widely applicable feasible assay for on-site analysis for cortisol in scales of fish is warranted.

Example 5

Quantification of Glucocorticoid Levels in Scales of Salmon

Method and Materials (see Example 1)

Experimental Set-up

Twelve samples of Chinook salmon (pre-stress and stressed (1 hour confinement)) were blindly analyzed for scale glucocorticoids in the framework of an extended collaboration with the USA regarding chronic stress in salmon.

Results

| Vial Number | Sample # | Pit tag # | Weight (g) | Sex | 20-Dihydrocortisone (ng/g) | Cortisone (ng/g) | Cortisol (ng/g) |
|---|---|---|---|---|---|---|---|
| 1 | 84 | 557 | 3875 | M | 8.924 | 20.861 | 98.174 |
| 2 | 85 | no tag | 4033 | M | 7.966 | 17.943 | 90.571 |
| 3 | 86 | 5293 | 2959 | F | 6.127 | 6.962 | 79.419 |
| 4 | 87 | 3224 | 6315 | F | 35.222 | 61.273 | 92.681 |
| 5 | 88 | 2510 | 3025 | M | 5.245 | 17.122 | 50.102 |
| 6 | 89 | 6820 | 5497 | F | 28.107 | 17.395 | 17.419 |
| 7 | 90 | 6484 | 3649 | F | 22.551 | 35.553 | 39.817 |
| 8 | 91 | 2109 | 4113 | F | 37.607 | 34.286 | 39.463 |
| 9 | 92 | 3485 | 4496 | M |  | 16.917 | 1.335 |
| 10 | 93 | 9611 | 4330 | F | 0.030 | 6.110 | 3.819 |
| 11 | 95 | 6334 | 4332 | F | 22.156 | 41.773 | 31.732 |
| 12 | 94 | 3464 | 5409 | F | 1.080 | 25.291 | 26.499 |

Example 6

Quantification of Glucocorticoid Levels in Scales of Seabream and Seabass

Method and Materials (see Example 1)
Experimental Set-up

The influence of conditioning of fish (day one versus day 3) was tested with seabass (*Dicentrarchus labrax*) and seabream (*Pagrus pagrus*).

Results

Seabass

| | | | Per treatment | | | | Overall | Overall |
|---|---|---|---|---|---|---|---|---|
| | | | no flash | | with flash | | ALL | ALL |
| | | Variable | | Standard | | Standard | | |
| Type | Day | Matrix/Parameter | Estimate | error | Estimate | error | Difference | P |
| META | 1 | Sexe | | | | | | |
| DATA | 1 | Length | 25.67 | 0.65 | 25.78 | 0.65 | 0.11670 | 0.8999 |
| | 1 | Weight | 178.62 | 16.85 | 186.25 | 16.85 | 7.63670 | 0.7516 |
| | 1 | BCS | 1.04 | 0.04 | 1.04 | 0.04 | −0.00715 | 0.8951 |
| | 3 | Sexe | | | | | | |
| | 3 | Length | 26.33 | 0.61 | 26.25 | 0.61 | −0.075 | 0.9319 |
| | 3 | Weight | 191.78 | 13.86 | 193.44 | 13.86 | 1.65830 | 0.9333 |
| | 3 | BCS | 1.03 | 0.02 | 1.05 | 0.02 | 0.01574 | 0.6597 |
| PLASMA | 1 | PL__Cortisol | 211.11 | 66.06 | 88.46 | 66.06 | −122.66 | 0.2103 |
| | 3 | PL__Cortisol | 151.55 | 49.19 | 223.84 | 47.10 | 72.28570 | 0.3006 |
| SCALE | 1 | OG__Amount of scale | 0.04 | 0.00 | 0.04 | 0.00 | −0.00368 | 0.2789 |
| OG | 1 | OG__Weight per scale | 0.00 | 0.00 | 0.00 | 0.00 | −0.00013 | 0.5434 |
| | 3 | OG__Amount of scale | 0.04 | 0.00 | 0.05 | 0.00 | 0.00620 | 0.1439 |
| | 3 | OG__Weight per scale | 0.00 | 0.00 | 0.00 | 0.00 | 0.00002 | 0.8984 |
| | 1 | OG__Cortisol per scale | 0.06 | 0.01 | 0.06 | 0.01 | −0.00348 | 0.8451 |
| | 1 | OG__Cortisone per scale | 0.03 | 0.01 | 0.04 | 0.01 | 0.00171 | 0.8114 |
| | 1 | OG__Reichstein's U per scale | 0.04 | 0.00 | 0.04 | 0.00 | −0.00409 | 0.3737 |
| | 3 | OG__Cortisol per scale | 0.04 | 0.00 | 0.02 | 0.00 | −0.01601 | 0.0050 |
| | 3 | OG__Cortisone per scale | 0.03 | 0.00 | 0.02 | 0.00 | −0.00678 | 0.2305 |
| | 3 | OG__Reichstein's U per scale | 0.03 | 0.00 | 0.02 | 0.00 | −0.00638 | 0.2573 |

Seabream

| | | | Per treatment | | | | Overall | Overall |
|---|---|---|---|---|---|---|---|---|
| | | | no flash | | with flash | | ALL | ALL |
| | | Variable | | Standard | | Standard | | |
| Type | Day | Matrix/Parameter | Estimate | error | Estimate | error | Difference | P |
| META | 1 | Sexe | | | | | | |
| DATA | 1 | Length | 23.04 | 0.25 | 23.21 | 0.25 | 0.16670 | 0.6455 |
| | 1 | Weight | 208.65 | 8.08 | 210.16 | 8.08 | 1.50750 | 0.8962 |

-continued

| | | | Per treatment | | | | Overall | Overall |
|---|---|---|---|---|---|---|---|---|
| | | | no flash | | with flash | | ALL | ALL |
| Type | Day | Variable Matrix/Parameter | Estimate | Standard error | Estimate | Standard error | Difference | P |
| | 1 | BCS | 1.70 | 0.04 | 1.68 | 0.04 | −0.02420 | 0.6640 |
| | 3 | Sexe | | | | | | |
| | 3 | Length | 22.75 | 0.45 | 23.75 | 0.45 | 1.00000 | 0.1301 |
| | 3 | Weight | 210.71 | 11.36 | 227.45 | 11.36 | 16.73580 | 0.3089 |
| | 3 | BCS | 1.82 | 0.09 | 1.68 | 0.09 | −0.1346 | 0.3052 |
| PLASMA | 1 | PL_Cortisol | 148.07 | 34.38 | 34.43 | 34.38 | −113.6300 | 0.0289 |
| | 3 | PL_Cortisol | 114.05 | 30.44 | 100.44 | 30.44 | −13.6037 | 0.7550 |
| SCALE | 1 | OG_Amount of scale | 0.03 | 0.00 | 0.03 | 0.00 | 0.00253 | 0.4644 |
| OG | 1 | OG_Weight per scale | 0.00 | 0.00 | 0.00 | 0.00 | 0.00006 | 0.5232 |
| | 3 | OG_Amount of scale | 0.03 | 0.00 | 0.03 | 0.00 | 0.00093 | 0.7586 |
| | 3 | OG_Weight per scale | 0.00 | 0.00 | 0.00 | 0.00 | −0.00015 | 0.1199 |
| | 1 | OG_Cortisol per scale | 0.03 | 0.01 | 0.03 | 0.01 | −0.00178 | 0.8070 |
| | 1 | OG_Cortisone per scale | 0.04 | 0.01 | 0.05 | 0.01 | 0.01826 | 0.2297 |
| | 1 | OG_Reichstein's U per scale | 0.05 | 0.01 | 0.04 | 0.01 | 0.01630 | 0.0441 |
| | 3 | OG_Cortisol per scale | 0.01 | 0.00 | 0.02 | 0.00 | 0.00710 | 0.2944 |
| | 3 | OG_Cortisone per scale | 0.08 | 0.02 | 0.04 | 0.02 | 0.04097 | 0.1581 |
| | 3 | OG_Reichstein's U per scale | 0.04 | 0.00 | 0.03 | 0.00 | −0.00913 | 0.0967 |

REFERENCES

A. References in Background Art

1. Baker, M. R., K. S. Gobush, and C. H. Vynne (2013). Review of factors influencing stress hormones in fish and wildlife. *J. Nat. Conserv.* 21:309-318.
2. Boonstra R. (2013). The ecology of stress: a marriage of disciplines. *Funct. Ecol.* 27:7-10.
3. O'Connor C. M., D. R. Norris, G. T. Crossin, and S. J. Cooke (2014). Biological carryover effects: linking common concepts and mechanisms in ecology and evolution. *Ecosphere* 5, art 28.
4. Richardson K. (2013). Anthropogenically-induced changes in the environment: effect of fisheries. ftp://ftp.fao.org/fi/document/reykjavik/pdf/16Richardson.pdf.
5. Consensus. Towards sustainable aquaculture in Europe. (2013) http://www.learneurope.eu/files/5813/7456/5881/Towards_sustainable_aquaculture_in_Europe.pdf.
6. Bush S. R., B. Belton, D. Hall, P. Vandergeest, and F. J. Murray, et al. (2013). Certify Sustainable Aquaculture? *Science* 341:1067-1068.
7. Diggles B. K., S. J. Cooke, J. D. Rose, and W. Sawynok (2011). Ecology and welfare of aquatic animals in wild capture fisheries. *Rev. Fish Biol. Fisheries* 21:739-765.
8. EFSA (2008). Scientific report of EFSA on Animal welfare aspects of husbandry systems for farmed common carp (Question No EFSA-Q-2006-148). Annex I to the *EFSA Journal* 843:1-81.
9. Bergqvist J., and S. Gunnarsson (2013). Finfish Aquaculture: Animal Welfare, the Environment, and Ethical Implications. *J Agric. Environ. Ethics* 26:75-99.
10. Anderson P. A., I. K. Berzins, F. Fogarty, H. J. Hamlin and L. J. Guillette Jr. (2011). Sound, stress, and seahorses: the consequences of a noisy environment to animal health. *Aquaculture* 311:129-138.
11. Anderson P. A. (2013). Acoustic characterization of seahorse tank environments in public aquaria: A citizen science project. *Aquacult Engineering* 54:72-77.
12. The Research Council of Norway (2009). Fish in research—environmental requirements and welfare indicators for fish. A review of research needs.
13. Wendelaar Bonga S. E. (1997). The stress response in fish. *Physiol. Rev.* 77: 591-626.
14. Barton B. A. (2002). Stress in fishes: a diversity of responses with particular reference to changes in circulating corticosteroids. *Integr. Comp. Biol.* 42:517-525.
15. Blas J., G. R. Bortolotti, J. L. Tella, R. Baos, and T. A. Marchant (2007). Stress response during development predicts fitness in a wild, long lived vertebrate. *Proc. Natl. Acad. Sci. U.S.A.* 104: 8880-8884.
16. Sapolsky R. M., L. M. Romero, and A. U. Munck (2000). How do glucocorticoids influence stress responses? Integrating permissive, suppressive, stimulatory, and preparative actions. *Endocr. Rev.* 21:55-89.
17. Cockrem J. F. (2013). Individual variation in glucocorticoid stress responses in animals. *Gen. Comp. Endocrinol.* 181:45-58.
18. McEwen B. S., and J. C. Wingfield (2003). The concept of allostasis in biology and biomedicine. *Horm. Behav.* 43:2-15.
19. Korte S. M., J. M. Koolhaas, J. C. Wingfield, and B. S. McEwen (2005). The Darwinian concept of stress: benefits of allostasis and costs of allostatic load and the trade-offs in health and disease. *Neurosci. Biobehav. Rev.* 29:3-38.
20. Overli O., C. Sorensen, K. G. T. Pulman, T. G. Pottinger, and W. Korzan et al. (2007). Evolutionary background for stress coping styles: Relationships between physiological, behavioral, and cognitive traits in non-mammalian vertebrates. *Neurosci. Biobehav. Rev.* 31:396-412.
21. Tellis M. S., D. Alsop, and C. M. Wood (2012). Effects of copper on the acute cortisol response and associated physiology in rainbow trout. *Comp. Biochem. Physiol. Part C: Pharmacol. Toxicol. Endocrinol.* 155:281-289.
22. Toorchi M., A. Bani, and H. Alizadehsabet (2012). Effects of salinity on osmoregulation and plasma cortisol levels of juvenile Caspian trout, *Salmo trutta caspius* Kessler, 1877. *J. Appl. Ichthyol.* 28:130-134.
23. Oliveira C. C. V., R. A. B. Blanco, V. O. Chereguini, I. Martin, and F. J. Sanchez-Vazquez (2013). Endocrine (plasma cortisol and glucose) and behavioral (locomotor and self-feeding activity) circadian rhythms in Senegalese sole (*Solea senegalensis* Kaup 1858) exposed to light/dark cycles or constant light. *Fish Physiol. Biochem.* 39:479-487.

24. Romano M. C., A. Z. Rodas, R. A. Valdez, S. E. Hernández, and F. Galindo et al. (2010). Stress in wildlife species: noninvasive monitoring of glucocorticoids. *Neuroimmunomodulation* 17:209-212.

25. Cook N. J. (2012). Review: Minimally invasive sampling media and the measurement of corticosteroids as biomarkers of stress in animals. *Can. J. Anim. Sci.* 92:227-259.

26. Small B. C. (2003). Anesthetic efficacy of metomidate and comparison of plasma cortisol responses to tricaine methanesulfonate, quinaldine and clove oil anesthetized channel catfish *Ictalurus punctatus*. *Aquaculture* 218:177-185.

27. Palić D., D. M. Herolt, C. B. Andreasen, B. W. Menzel, and J. A. Roth (2006). Anesthetic efficacy of tricaine methanesulfonate, metomidate and eugenol: Effects on plasma cortisol concentration and neutrophil function in fathead minnows (*Pimephales promelas* Rafinesque, 1820). *Aquaculture* 254:675-685.

28. Simontacchi C., C. Poltronieri, C. Carraro, D. Bertotto, and G. Xiccato, et al. (2008). Alternative stress indicators in sea bass *Dicentrarchus labrax*, L. *J. Fish Biol.* 72:747-752.

29. Bertotto D., C. Poltronieri, E. Negrato, D. Majolini, and G. Radaelli, et al. (2010). Alternative matrices for cortisol measurement in fish. *Aquacult. Res.* 41:1261-1267.

30. Lupica S. J., and J. W. Turner Jr. (2009). Validation of enzyme-linked immunosorbent assay for measurement of fecal cortisol in fish. *Aquacult. Res.* 40:437-441.

31. Ellis T., J. D. James, C. Stewart, and A. P. Scott (2004). A non-invasive stress assay based upon measurement of free cortisol released into the water by rainbow trout. *J. Fish Biol.* 65:1233-1252.

32. Takahara T., H. Yamanaka, A. A. Suzuki, M. N. Honjo, and T. Minamoto et al. (2011). Stress response to daily temperature fluctuations in common carp, *Cyprinus carpio* L. *Hydrobiologia* 675:65-73.

33. Close D. A., S. S. Yuna, S. D. McCormick, A. J. Wildbill, and L. Weiming (2010). 11-Deoxycortisol is a corticosteroid hormone in the lamprey. *Proc. Natl. Acad. Sci. U.S.A.* 107:13942-13947.

34. Cadrin S. X., L. A. Kerr, and S. Mariani (2013). *Stock Identification Methods: Applications in Fishery Science*, Academic Press.

35. Tserpes G., and N. Tsimenides (1995). Determination of age and growth of swordfish, *Xiphias gladius* L., 1758, in the eastern Mediterranean using anal-fin spines. *Fish Bull.* 93:594-602.

36. Kawajiri M., and K. Yamahira (2011). Genetic and thermal effects on the latitudinal variation in the timing of fin development of a fish *Oryzias latipes*. *Environ. Biol. Fishes* 92:285-293.

37. Payan P., H. De Pontual, A. Edeyer, G. Borelli, and G. Boeuf, et al. (2004). Effects of stress on plasma homeostasis, endolymph chemistry, and check formation during otolith growth in rainbow trout (*Oncorhynchus mykiss*). *Can. J. Fish Aquat. Sci.* 61:1247-1255.

38. Bortolotti G. R., T. A. Marchant, J. Blas, and S. Cabezas (2009a). Tracking stress: localization, deposition and stability of corticosterone in feathers. *J. Exp. Biol.* 212:1477-1482.

39. Cirimele V., P. Kintz, V. Dumestre, J. P. Goulle, and B. Ludes 2000. Identification of ten corticosteroids in human hair by liquid chromatography-ionspray mass spectrometry. *Forensic Sci. Int.* 107:381-388.

40. Schönbörner A. A., G. Boivin, and C. A. Baud (1979). The mineralization processes in teleost fish scales. *Cell Tissue Res.* 202:203-212.

41. Metz J. R., E. De Vrieze, E. J. Lock, I. E. Schulten, and G. Flik (2012). Elasmoid scales of fishes as model in biomedical bone research. *J. Appl. Ichthyol.* 28:382-387.

42. Persson P., J. M. Shrimpton, S. D. McCormick, and B. T. Bjornsson (2000). The presence of high-affinity, low-capacity estradiol-17b binding in rainbow trout scale indicates a possible endocrine route for the regulation of scale resorption. *Gen. Comp. Endocrinol.* 120:35-43.

43. Pinto P. I. S., M. D. Estevao, B. Redruello, S. M. Socorro, A. V. Canario, and D. M. Power (2009). Immunohistochemical detection of estrogen receptors in fish scales. *Gen. Comp. Endocrinol.* 160:19-29.

B. References in Description of Application

(44) Bury N. R., and A. Sturm (2007). *Gen. Comp. Endocrinol.* 153:47-56.

(45) http://www.chemspider.com/Chemical-Structure.5932.html

(46) Cirillo N., S. S. Prime (2011). *J. Cell. Biochem.* 112:1499-1505.

(47) Raul J. S., Vincent Cirimele, Bertrand Ludes, and Pascal Kintz (2004). *Clin. Biochem.* 37:1105-1111.

(48) Gow R., S. Thomson, M. Rieder, S. Van Uum, and G. Koren (2010). *Forensic Sci. Int.* 196:32-37.

(49) Sugawara E. K., and L. Verreschi (2010). *Quim. Nova* 33:447-450.

(50) Yajie Xiao Y., S. W. Chan, M. Hu, T. T. W. Chu, B. S. P. Fok, E. W. M. Poon, and B. Tomlinson (2012). *Chromatographia* 75:169-173.

(51) Gao W., Q. Xie, J. Jin, T. Qiao, H. Wang, L. Chen, H. Deng, and Z. Lu (2010). *Clin. Biochem.* 43:677-682.

(52) Shibata N., T. Hayakawa, K. Takada, N. Hoshino, T. Minouchi, and A. Yamaji (1998). *J. Chromatogr. B.* 706:191-199.

(53) Shibasakia H., H. Nakayamaa, T. Furutaa, Y. Kasuyaa, M. Tsuchiyab, A. Soejimab, Yamadab, and T. Nagasawab (B. 2008). *J. Chromatogr.* 870:164-169.

(54) Ahmadkhaniha R., A. Shafiee, N. Rastkari, M. R. Khoshayand, and F. Kobarfard (B. 2010). *J. Chromatogr.* 878:845-852.

(55) O'Connor E. A., T. G. Pottinger, and L. U. Sneddon (2011). *Fish Physiol. Biochem.* 37:461-469.

(56) Benjamin Costas B., L. E. C. Conceição, C. Aragão, J. A. Martos, I. Ruiz-Jarabo, J. M. Mancera, and A. Afonso (2011). *Aquaculture* 316:68-76.

(57) Tellis M. S., D. Alsop, and C. M. Wood (2012). *Comp. Bioch. Fysiol.* 155:281-289.

(58) Toorchi M., A. Bani, and H. Alizadehsabet (2012). *J. Appl. Ichthyol.* 28:130-134

(59) Sun K., N. Ramgir, and S. Bhansali (B. 2008). *Sens. Actuators* 133:533-537.

(60) Mitchell J. S., T. E. Lowe, and J. R. Ingram (2009). *Analyst* 134:380-386.

C. References in Example 1

(61) Commission Decision No. 2002/657/EC, Concerning the performance of analytical methods and the interpretation of results. *Off. J. Eur. Commun.* 2002.

(62) EN ISO/IEC 17025:2005, General requirements for the competence of testing and calibration laboratories. *CEN/CENELEC*, 2005.

(63) ISO/DIS 5725:1994, *Accuracy of Measurement Methods and Results* 1994.

(64) Barnett V. and T. Lewis. *Outliers in Statistical Data* 3rd ed., 1994.
(65) Ellis T., M. B. Sanders, and A. P. Scott (2013). *Wiener Tierärztliche Monatsschrift* 100:255-269.
(66) McWhinney B. C., G. Ward, and P. E. Hickman (1996). *Clin. Chem.* 42(6):979-981.
(67) Flor S., S. Lucangioli, M. Contin, and V. Tripodi (2010). *Electrophoresis* 31:3305-3313.
(68) Heistermann M., R. Palme, and A. Ganswindt (2006). *Am. J Primatol.* 68:257-273.
D) References in Example 2
(69) Gorissen M., N. J. Bernier, R. Manuel, S. de Gelder, J. R. Metz, M. O. Huising, and G. Flik (2012). *Gen. Comp. Endocrinol.* 178:75-81.
E) References in Example 3
(69). Gorissen M., N. J. Bernier, R. Manuel, S. de Gelder, and J. R. Metz et al. (2012). Recombinant human leptin attenuates stress axis activity in common carp (*Cyprinus carpio* L.). *Gen. Comp. Endocrinol.* 178:75-81.
(70). Schram E., J. A. C. Roques, W. Abbink, T. Spanings, and P. de Vries, et al. (2010). The impact of elevated water ammonia concentration on physiology, growth and feed intake of African catfish (*Clarias gariepinus*). *Aquaculture* 306:108-115.
(71). Cohen S. A., and L. Sideman (1979). Modification of the o-cresolphtalein complexone method for determining calcium. *Clin. Chem.* 25:1519-1520.
(72). De Vrieze, E. et al. (2014). Prednisolone induces osteoporosis-like phenotype in regenerating zebrafish scales. *Osteoporosis Int.* 25:567-578.
(73). Nash R. D. M., A. H. Valencia, and A. J. Geffen (2006). The origin of Fulton's condition factor—setting the record straight. *Fisheries* 31:236-238.
(74). Dang Z. C., P. H. M. Balm, G. Flik, S. E. Wendelaar Bonga, and R. A. C. Lock (2000). Cortisol increases $Na^+/K^+$-ATPase density in plasma membranes of gill chloride cells in the freshwater tilapia *Oreochromis mossambicus*. *J. Exp. Biol.* 203:2349-2355.
(75). Metz J. R., E. De Vrieze, E. J. Lock, I. E. Schulten, and G. Flik (2012). Elasmoid scales of fishes as model in biomedical bone research. *J. Appl. Ichthyol.* 28:382-387.
F) References in Example 4
(69). Gorissen M., N. J. Bernier, R. Manuel, S. de Gelder, and J. R. Metz et al. (2012). Recombinant human leptin attenuates stress axis activity in common carp (*Cyprinus carpio* L.). *Gen. Comp. Endocrinol.* 178:75-81.
(70). Schram E., J. A. C. Rogues, W. Abbink, T. Spanings, and P. de Vries et al. (2010). The impact of elevated water ammonia concentration on physiology, growth and feed intake of African catfish (*Clarias gariepinus*). *Aquaculture* 306:108-115.
(71). Cohen S. A., and L. Sideman (1979). Modification of the o-cresolphtalein complexone method for determining calcium. *Clin. Chem.* 25:1519-1520.
(73). Nash R. D. M., A. H. Valencia, and A. J. Geffen (2006). The origin of Fulton's condition factor—setting the record straight. *Fisheries* 31:236-238.

The invention claimed is:

1. An in vitro method of quantifying the level of chronic stress in a fish, the method comprising:
obtaining at least one scale from the fish,
extracting glucocorticoids from said scale,
purifying the glucocorticoids extracted from said scale,
quantifying said purified glucocorticoids, and
correlating said quantified glucocorticoids with a level of chronic stress.

2. The method according to claim 1, wherein the glucocorticoids comprise a glucocorticoid selected from the group consisting of cortisol, corticosterone, 17α-hydroxyprogesterone, 11-deoxycortisol, 11-deoxycorticosterone, cortisone, 20-dihydrocortisone, tetrahydrocortisol, and/or tetrahydrocortisone.

3. The method according to claim 1, wherein the fish belong to the infraclass of Teleostei.

4. The method according to claim 1, wherein said obtaining at least one scale from the fish is obtaining between 40 and 80 scales from the fish.

5. The method according to claim 1, wherein said extracting glucocorticoids is undertaken by adding utilizing methanol as an extraction solvent.

6. The method according to claim 5, wherein said extraction with methanol is followed by a solid phase extraction.

7. The method according to claim 1, wherein said quantifying of extracted glucocorticoids is undertaken by
liquid chromatography coupled to tandem mass spectrometry,
high performance liquid chromatography coupled to ultraviolet, diode array or fluorescence detection,
gas chromatography,
a radio immunoassay,
an enzymatic immunoassay or
a sensor based technique.

8. The method according to claim 7, wherein said liquid chromatography coupled to tandem mass spectrometry is ultra-performance liquid tandem mass spectrometry.

9. The method according to claim 7, wherein said immunoassay is a radio immunoassay or an enzyme immunoassay.

10. A method of quantifying a fish's level of chronic stress, the method comprising:
utilizing fish scales sampled from the fish to quantify the level of chronic stress of the fish.

11. The method according to claim 10 wherein said quantification is undertaken by a method comprising:
obtaining at least one scale from the fish,
extracting glucocorticoids from the scale,
purifying the glucocorticoids extracted from the scale,
quantifying the purified glucocorticoids, and
correlating the quantified glucocorticoids with a level of chronic stress.

12. A method of quantifying a fish's level of chronic stress, the method comprising:
utilizing a spine, a ray of a fin, or an otolith sampled from the fish to quantify the level of chronic stress of the fish.

13. An in vitro method of quantifying the level of chronic stress in a fish, the method comprising:
obtaining at least one spine, ray of a fin, or otolith from the fish,
extracting glucocorticoids from said spine, ray of a fin, or otolith,
purifying the glucocorticoids extracted from said spine, ray of a fin, or otolith,
quantifying said purified glucocorticoids, and
correlating said quantified glucocorticoids with a level of chronic stress in the fish.

* * * * *

UNITED STATES PATENT AND TRADEMARK OFFICE
CERTIFICATE OF CORRECTION

PATENT NO. : 9,638,703 B2  
APPLICATION NO. : 15/105550  
DATED : May 2, 2017  
INVENTOR(S) : Johan Aerts and Sarah De Saeger Page 1 of 1

It is certified that error appears in the above-identified patent and that said Letters Patent is hereby corrected as shown below:

In the Specification

| | | |
|---|---|---|
| Column 3, | Line 44, | change "of atp1a1a in" to --of atp1a1a in-- |
| Column 3, | Line 53, | change "relative colla1 expression" to --relative col1a1 expression-- |
| Column 9, | Line 50, | change "are lust or damaged." to --are lost or damaged.-- |
| Column 10, | Line 37, | change "0.5 µL, 2.5 µL," to --0.5 µL, 1 µL, 2.5 µL,-- |
| Column 15, | Line 1, | change "in 100 µt was" to --in 100 µL was-- |
| Column 16, | Line 7, | change "the carryover from" to --the carry over from-- |
| Column 19, | Line 5, | change "(Abeam);" to --(Abcam);-- |
| Column 19, | Line 10, | change "100 µblocking" to --100 µL blocking-- |
| Column 19, | Lines 20-21, | change "(PerkinElmer. USA," to --(PerkinElmer, USA,-- |
| Column 19, | Line 26, | change "HISAFEO-3" to --HISAFE®-3-- |
| Column 20, | Line 46, | change "using eef1al rps5" to --using eef1a1 rps5-- |
| Column 22, | Line 19, | change "of colla1 was" to --of col1a1 was-- |
| Column 22, | Line 25, | change "similar colla1 expression" to --similar col1a1 expression-- |

In References

| | | |
|---|---|---|
| Column 30, | Line 3, | change "40. Schönbömer" to --40. Schönbörner-- |
| Column 31, | Line 47, | change "Rogues" to --Roques-- |

In the Claims

| | | | |
|---|---|---|---|
| Claim 5, | Column 32, | Line 16, | change "by adding utilizing" to --by utilizing-- |
| Claim 11, | Column 32, | Line 39, | change "claim 10 wherein" to --claim 10, wherein-- |

Signed and Sealed this  
Twenty-third Day of January, 2018

Joseph Matal  
*Performing the Functions and Duties of the*  
*Under Secretary of Commerce for Intellectual Property and*  
*Director of the United States Patent and Trademark Office*